(12) United States Patent
Yang et al.

(10) Patent No.: US 10,792,108 B2
(45) Date of Patent: Oct. 6, 2020

(54) ATTACHMENTS FOR TRACKING HANDHELD IMPLEMENTS

(71) Applicant: 7D SURGICAL INC., Toronto (CA)

(72) Inventors: Victor X. D. Yang, North York (CA); Peter Siegler, Toronto (CA); Adrian Mariampillai, Toronto (CA); Beau Anthony Standish, Toronto (CA); Michael Leung, Markham (CA)

(73) Assignee: 7D SURGICAL INC., Toronto, ON (CA)

( * ) Notice: Subject to any disclaimer, the term of this patent is extended or adjusted under 35 U.S.C. 154(b) by 782 days.

(21) Appl. No.: 15/462,493

(22) Filed: Mar. 17, 2017

(65) Prior Publication Data

US 2017/0252109 A1 Sep. 7, 2017

Related U.S. Application Data

(63) Continuation of application No. 14/412,464, filed as application No. PCT/CA2013/050512 on Jul. 3, 2013, now Pat. No. 10,034,713.

(Continued)

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/064* (2013.01); *A61B 17/1703* (2013.01);
(Continued)

(58) Field of Classification Search
CPC ............ A61B 17/1703; A61B 17/1757; A61B 19/5244; A61B 2017/00477; A61B 2034/2055; A61B 2034/2065; A61B 2090/364; A61B 2090/3937; A61B 2090/3941; A61B 2090/3983; A61B 34/20; A61B 5/064; A61B 90/39
See application file for complete search history.

(56) References Cited

U.S. PATENT DOCUMENTS

| 5,888,200 A * | 3/1999 | Walen ................ A61B 17/1622 606/167 |
| 2005/0049485 A1* | 3/2005 | Harmon ................ A61B 90/39 600/429 |
| 2007/0260257 A1* | 11/2007 | Phan ................ A61B 17/1617 606/84 |

* cited by examiner

*Primary Examiner* — Mark D Remaly
(74) *Attorney, Agent, or Firm* — Hill & Schumacher

(57) ABSTRACT

Devices and systems are provided for tracking a position and orientation of a handheld implement, such that the handheld implement may be trackable with an overhead tracking system. A support member secures one or more markers relative to a longitudinal portion of the handheld implement, and a marker plane containing the markers is orientated an angle relative to a longitudinal axis of the longitudinal portion. A marker assembly may include a support member for supporting the markers, and a connector for removably attaching the marker assembly to one or more handheld implements. The marker assembly may be configured to be removably attachable to a plurality of connection adapters, where each connection adapter is further connectable to a handheld implement, optionally at a calibrated position, such that a single connection adapter can be optionally employed to track a plurality of handheld implements. The handheld implement may be a medical instrument.

23 Claims, 32 Drawing Sheets

Related U.S. Application Data

(60) Provisional application No. 61/667,714, filed on Jul. 3, 2012.

(51) Int. Cl.
*A61B 17/17* (2006.01)
*A61B 90/00* (2016.01)
*A61B 17/00* (2006.01)

(52) U.S. Cl.
CPC .......... *A61B 17/1757* (2013.01); *A61B 90/39* (2016.02); *A61B 2017/00477* (2013.01); *A61B 2034/2055* (2016.02); *A61B 2034/2065* (2016.02); *A61B 2090/364* (2016.02); *A61B 2090/3937* (2016.02); *A61B 2090/3941* (2016.02); *A61B 2090/3983* (2016.02)

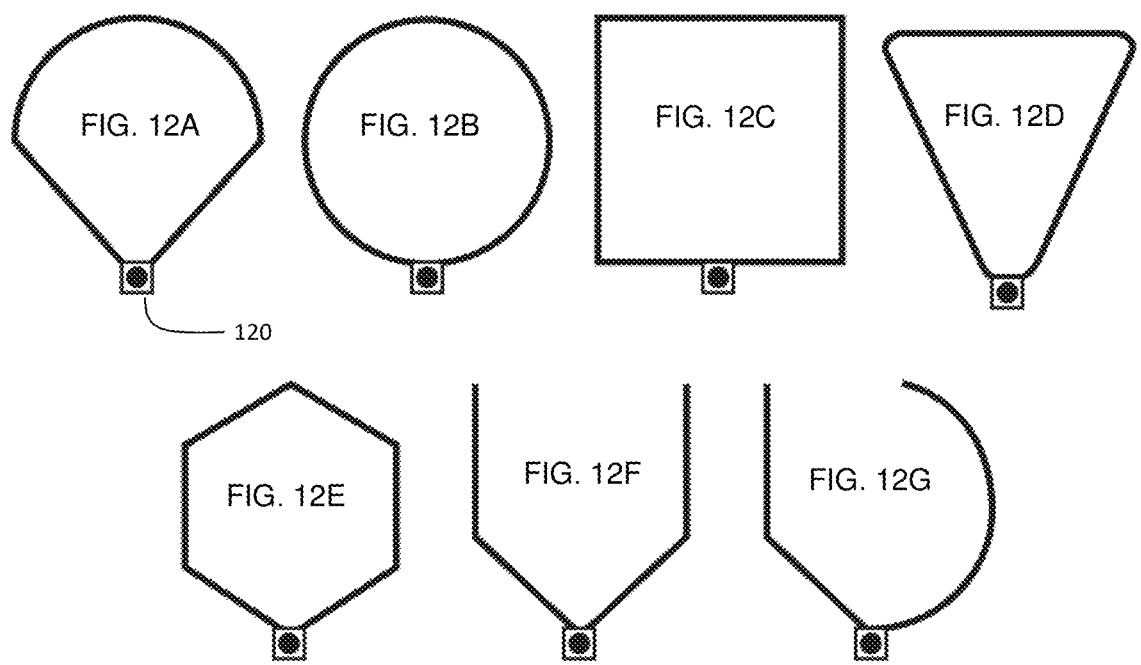

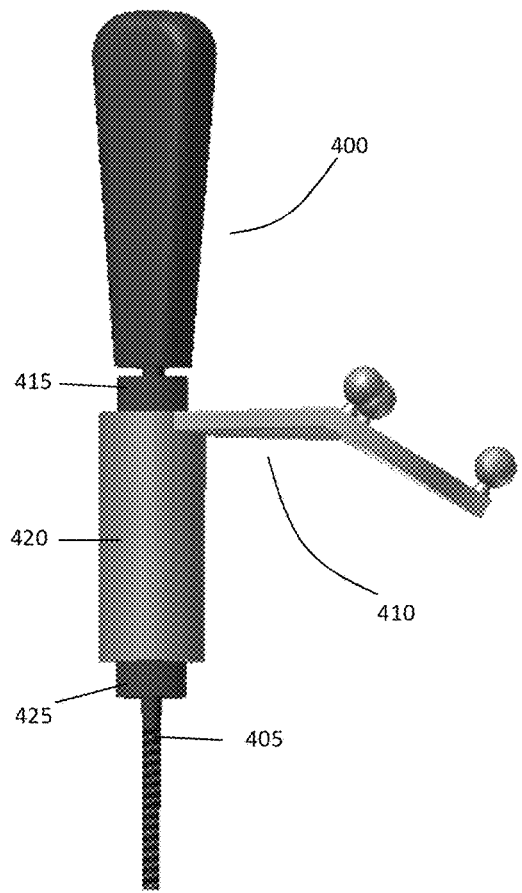
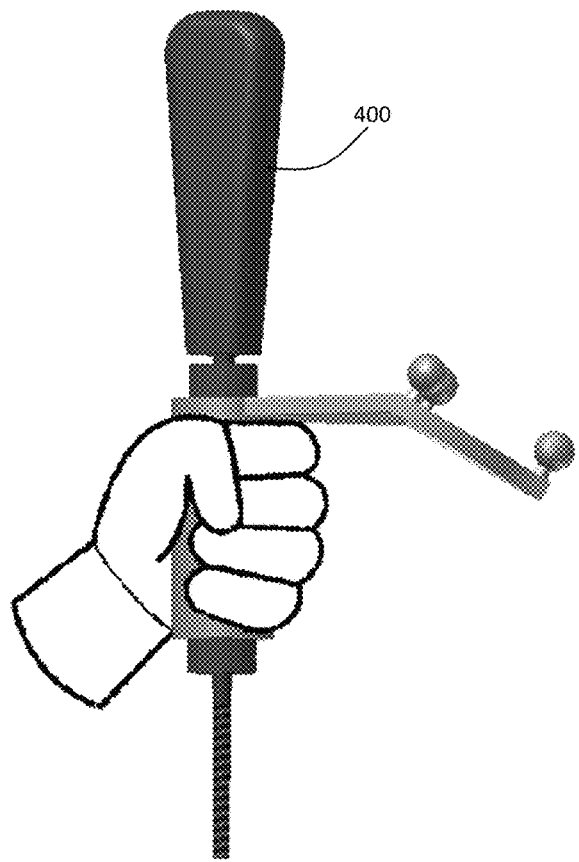
FIG. 16A
FIG. 16B

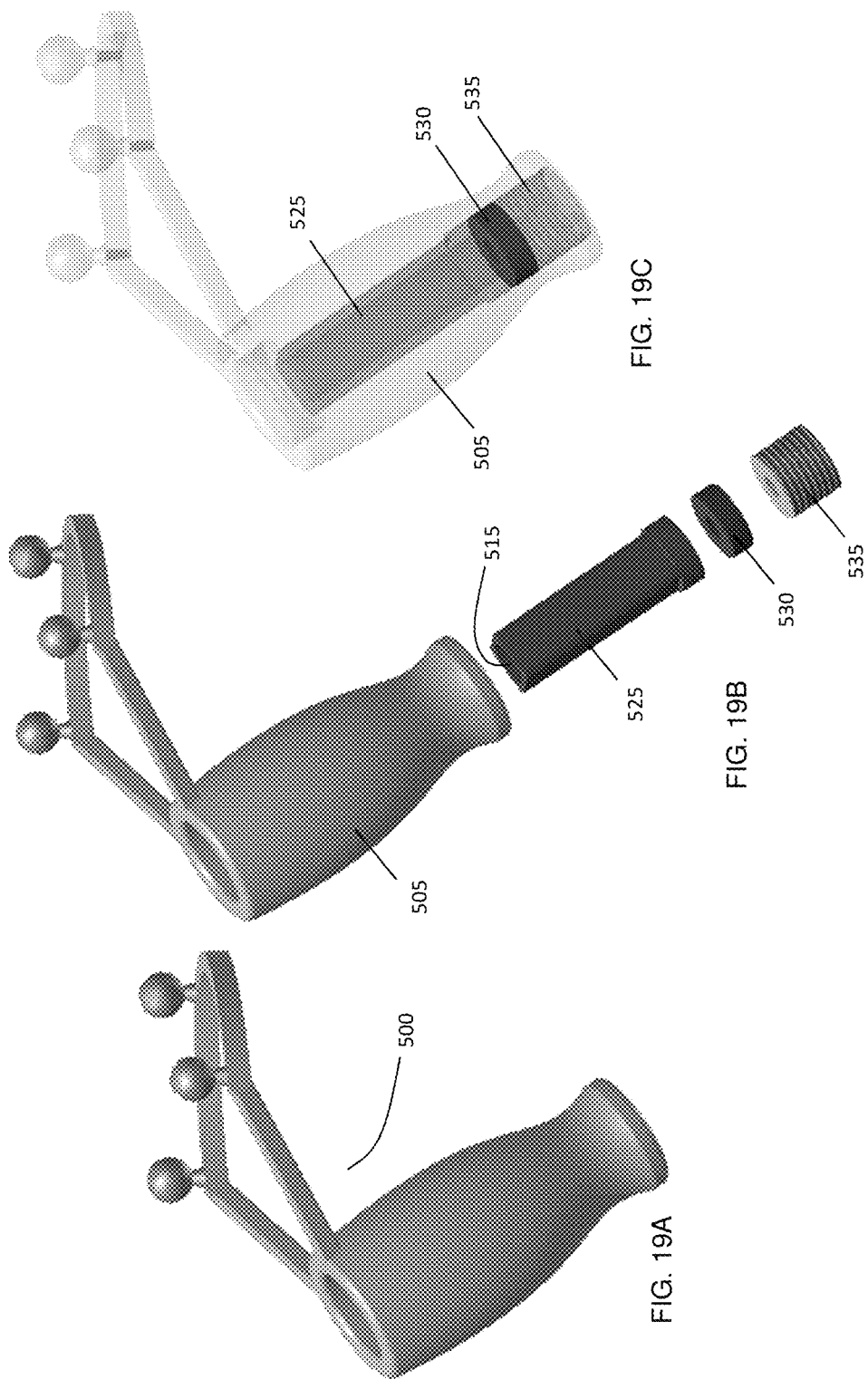

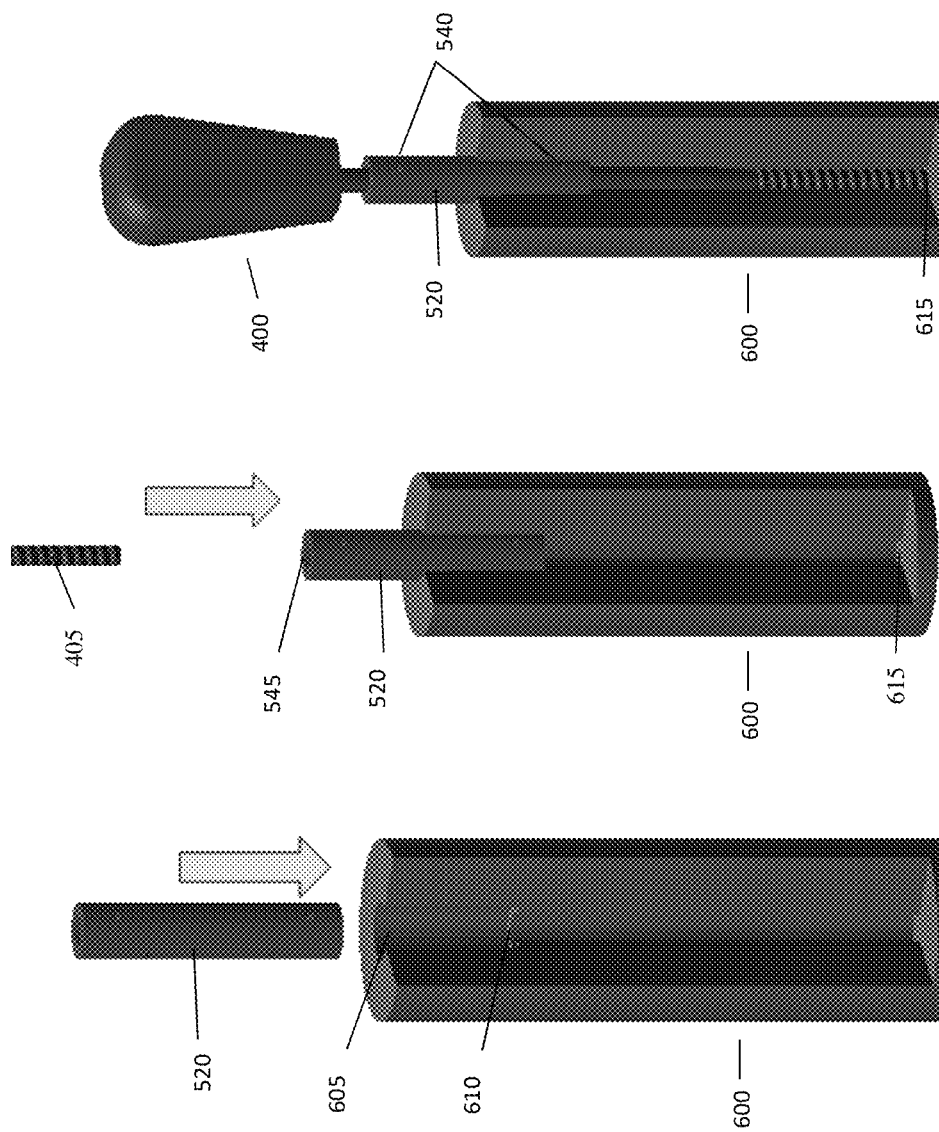

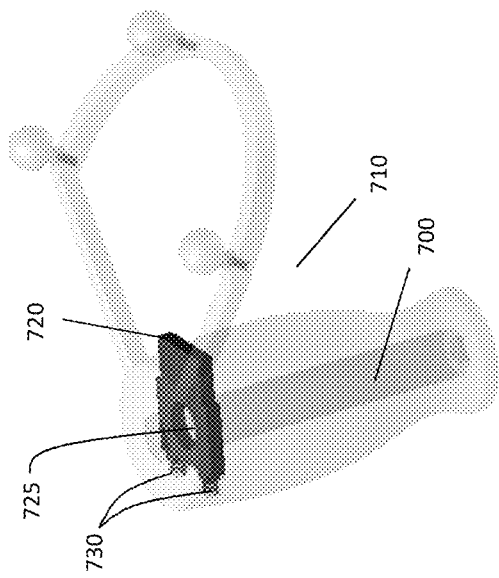
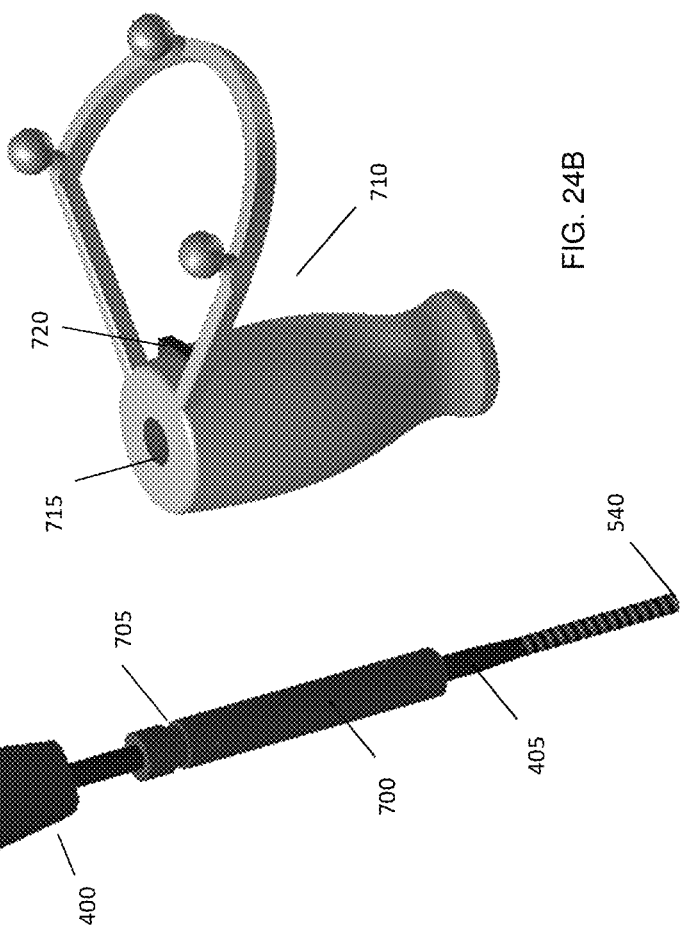
FIG. 24C
FIG. 24B
FIG. 24A

ATTACHMENTS FOR TRACKING HANDHELD IMPLEMENTS

CROSS-REFERENCE TO RELATED APPLICATION

This application is a Continuation of a National Phase application Ser. No. 14/412,464, filed Jan. 2, 2015, claiming the benefit of PCT/CA2013/050512, filed on Jul. 3, 2013 in English, which further claims priority to U.S. Provisional Application No. 61/667,714, titled "ATTACHMENTS FOR TRACKING HANDHELD IMPLEMENTS" and filed on Jul. 3, 2012, the entire contents of which are incorporated herein by reference.

BACKGROUND

The present disclosure relates to guidance and tracking systems for tracking handheld implements, such as medical instruments. More particularly, the present disclosure relates to active and passive marker arrangements for surgical guidance and tracking of medical instruments.

Surgical guidance enables surgeons to localize the position of surgical instruments relative to the human body without having full visual access during surgery. Surgical guidance is routinely used in surgeries of the spine, brain, hip or other organs.

In general, surgical guidance consists of two steps: The first step includes the acquisition of a three dimensional (3D) representation of relevant portion of the body. This step may involve a single or multiple imaging modalities such as computer tomography (CT), magnetic resonance tomography (MRT), positron emission tomography (PET) and ultrasound (US). The 3D representation may be acquired before and/or during the surgical procedure. In the second step, the spatial position of the body and the spatial relation of the surgical instruments to the position of the body are tracked during the surgery. The spatial position of the body is correlated to its 3D representation using specific image registration techniques. After registration, the spatial position of the surgical instruments can be displayed with a 3D representation of the body for the surgeon.

Typically, optical-based systems are used for the tracking of the spatial positions during the surgery. These systems are based on two cameras that detect the positions of at least three markers attached to the tracked surgical instruments (for example, mounted with LEDs as disclosed in U.S. Pat. No. 5,921,992, or mounted with reflective probes as disclosed in U.S. Pat. No. 6,061,644).

There are many possible designs for the attachment of these markers to surgical instruments that include a longitudinal shaft (for example, U.S. Pat. Nos. 6,021,343, 7,226, 456 B2, 6,556,857 B1, 7,166,114 B2, and 2002/0077540 A1). However, most of these designs include a common characteristic that the cameras of the optical tracking system are oriented to view the side of the shaft of the surgical instruments. The markers are therefore aligned along the instrument shaft.

In other applications, the tracking system may be oriented directly above the surgical incision, such that the tracking system "looks" into the incision. These applications include arrangements for which the tracking system is integrated into the surgical lighting system (for example, U.S. Pat. No. 7,224,472), or arrangements for which the tracking system is integrated into a system for performing optical topology imaging of anatomy within the incision (for example, U.S. Pat. Nos. 5,531,520 and 5,999,840 and PCT Patent Application PCT/CA2011/050257).

SUMMARY

Devices and systems are provided for tracking a position and orientation of a handheld implement, such that the handheld implement may be trackable with an overhead tracking system. A support member secures one or more markers relative to a longitudinal portion of the handheld implement, and a marker plane containing the markers is orientated an angle relative to a longitudinal axis of the longitudinal portion. A marker assembly may include a support member for supporting the markers, and a connector for removably attaching the marker assembly to one or more handheld implements. The marker assembly may be configured to be removably attachable to a plurality of connection adapters, where each connection adapter is further connectable to a handheld implement, optionally at a calibrated position, such that a single connection adapter can be optionally employed to track a plurality of handheld implements. The handheld implement may be a medical instrument.

Accordingly, in a first aspect, there is a marker assembly for locating a handheld implement, the marker assembly comprising: a support member; at one or more tracking markers affixed to the support member, the tracking markers defining a marker plane; and a connector configured to removably attach the support member to a longitudinal portion of the handheld implement, the longitudinal portion defining a longitudinal axis; wherein the marker plane is not parallel to the longitudinal axis when the marker assembly is secured to the handheld implement; and wherein the one or more tracking markers are suitable for locating a three-dimensional position and orientation of the handheld implement when the marker assembly is secured to the handheld implement.

In another aspect, there is provided an interchangeable marker system for tracking a plurality of handheld implements, the system comprising: a plurality of connection adapters, wherein each connection adapter is attached to, or attachable to, a longitudinal shaft of one of the handheld implements, and wherein the connection adapters have a common outer cross-section; and a marker assembly comprising: a longitudinal body having an inner bore suitable for receiving one of the connection adapters; a connection mechanism for connecting the longitudinal body to the connection adapter; a support member connected to the longitudinal body; and one or more tracking markers affixed to the support member, the tracking markers defining a marker plane; wherein the marker assembly is removably attachable to each of the handheld implements through the connection adapters; and wherein the one or more tracking markers are suitable for locating a three-dimensional position and orientation of the handheld implement when the marker assembly is secured to the handheld implement.

In another aspect, there is provided a guidance system for tracking one or more handheld implements, the guidance system comprising: a marker assembly as described above; a tracking system configured to detect a signal associated with each tracking marker, wherein the tracking system is positioned in a substantially overhead configuration; and a processor configured to receive the signals and to calculate a relative position and orientation of the handheld implement based on the signals, when the marker assembly is secured to the handheld implement.

In another aspect, there is provided a trackable handheld device comprising: a handheld implement comprising a longitudinal shaft, the longitudinal shaft defining a longitudinal axis; a support member connected to the longitudinal shaft; and one or more tracking markers affixed to the support member, the tracking markers defining a marker plane; wherein the marker plane is not parallel to the longitudinal axis, such that the tracking markers are visible to an overhead tracking system during use of the handheld implement; and wherein the one or more tracking markers are suitable for locating a three-dimensional position and orientation of the handheld implement by the overhead tracking system.

In another aspect, there is provided a trackable tool system comprising: a plurality of exchangeable tool extensions, each exchangeable tool extension having a proximal portion, a distal functional end, and a longitudinal axis; a handheld body adapted to detachably secure each exchangeable tool extension at the proximal portion thereof, such that one exchangeable tool extension may be secured to the handheld body at any given time; a support member connected to the handheld body; and one or more tracking markers affixed to the support member, the tracking markers defining a marker plane; wherein each exchangeable tool extension has common length, such that when a first exchangeable tool extension is replaced with a second exchangeable tool extension, the one or more tracking markers are suitable for locating a three-dimensional position of the distal functional end of the second exchangeable tool extension and an orientation the second exchangeable tool extension by a tracking system without recalibration.

In another aspect, there is provided a guidance system for tracking one or more handheld implements, the guidance system comprising: a trackable handheld device as described above; a tracking system configured to detect a signal associated with each tracking marker, wherein the tracking system is positioned in a substantially overhead configuration; and a processor configured to receive the signals and to calculate a relative position and orientation of the handheld implement based on the signals, when the support member is secured to the handheld implement.

In another aspect, there is provided a guidance system for tracking one or more handheld implements, the guidance system comprising: an interchangeable marker system as described above; a tracking system configured to detect a signal associated with each tracking marker, wherein the tracking system is positioned in a substantially overhead configuration; and a processor configured to receive the signals and to calculate a relative position and orientation of the handheld implement based on the signals, when the marker assembly is secured to the handheld implement.

A further understanding of the functional and advantageous aspects of the disclosure can be realized by reference to the following detailed description and drawings.

BRIEF DESCRIPTION OF DRAWINGS

Embodiments will now be described, by way of example only, with reference to the drawings, in which:

FIGS. 12A-12G list examples of open and closed ring shapes for the marker assembly.

FIG. 16A shows the example marker assembly attached to a rotatable medical instrument, where FIG. 16B shows that full rotation of the medical instrument is possible while the marker assembly is held.

FIGS. 19A-19C shows detailed views of the marker assembly shown in FIGS. 18A-18C, showing FIG. 19A an external view of the assembled marker assembly, FIG. 19B an exploded assembly view, and FIG. 19C a semi-transparent view showing the internal components.

FIGS. 22A-22C illustrate the steps to secure the connection adapter on the shaft of the medical instrument using the calibration tool, including FIG. 22A placing the connection adapter inside the top bore of the calibration tool, FIG. 22B inserting the shaft of the medical instrument through the connection adapter, and FIG. 22C tightening the connection adapter to the instrument shaft when the shaft tip touches the bottom of the calibration tool.

FIGS. 24A-24C show components of an example embodiment of a marker assembly that allows the marker assembly to be removably attached to different medical instruments, showing FIG. 24A the connection adapter which is attached to each tracked medical instrument, FIG. 24B the marker assembly with mechanical clamping mechanism, and FIG. 24C a semi-transparent view of the marker assembly to show the clamping mechanism inside the handle.

FIG. 28A During use, the spring collet clicks on the notch in the locking feature of the inserted tool extension. FIG. 28B For release, the outside cylinder is slid, spreading the spring collet with a coned notch.

DETAILED DESCRIPTION

Figure 1A:
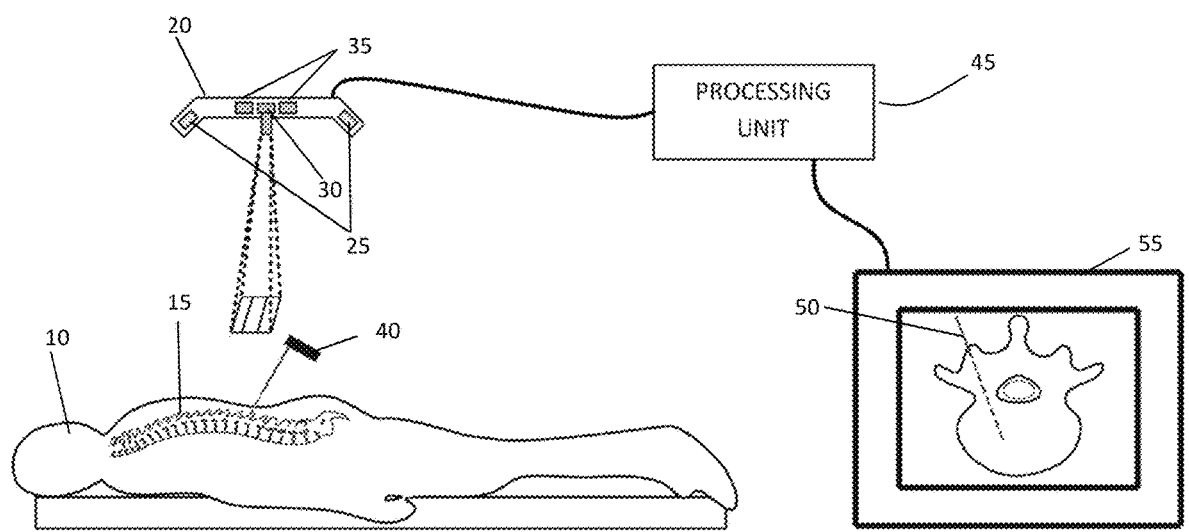
FIG. 1A shows a schematic of an example surgical guidance system that includes an overhead integrated tracking system that employs structured light surface detection for image registration and optical tracking of medical instruments and medical devices with marker attachments, FIG. 1B a conventional marker arrangement on a medical instrument for optical tracking from the side direction, and FIG. 1C an illustration of the line of sight obstruction problem that would occur with such an arrangement when employed with overhead tracking.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. It should be understood that the order of the steps of the methods disclosed herein is immaterial so long as the methods remain operable. Moreover, two or more steps may be conducted simultaneously or in a different order than recited herein unless otherwise specified.

As used herein, the phrase "medical instrument" refers to any type of instrument or tool, which is used during surgery, diagnosis or other medical examinations or procedures and has a longitudinal axis. The longitudinal axis may be defined by a longitudinal shaft. Possible examples are surgical instruments such as awls, screwdrivers, pedicle finders, and cutters used for example in spinal surgeries. Further examples are drills and other tools in dentistry, needles for biopsy, and applicators for thermal therapies (including radiofrequency (RF) ablation, cryoablation, laser induced thermal therapy (LIT), or microwave ablation). One example for a non-surgical tool is a pointing stylus in image-guided procedures. Other non-limiting examples of surgical instruments include a section tip, shunt passer, scalpel/knife, scissor, forceps, bipolar, hook, retractor, dissector, drill, kerrison rongeur, osteotome, needle, (micovascular) micro Doppler probe, screwdriver, monopolar, cusa, dilators, probe/stylus, bone impactor, K-wire, taps, speculum, and curette.

As used herein, the term "tracking system" is any device that allows the detection of the position and orientation of an object in three dimensions (3D). As a possible example, an optical tracking system operating with visual or infrared light may include stereo cameras to detect the positions of passive optical markers (e.g. reflective spheres) and/or active optical markers (e.g. light emitting diodes (LEDs)). Other non-limiting examples of tracking systems include electromagnetic tracking systems and structured light tracking systems.

As used herein, the term "marker" refers to a locating indicator that may be affixed or otherwise connected to a handheld implement, patient, subject, instrument, tool, or other component of a surgical system or surgical field, and which is detectable by a tracking system for use determining a position or location. A marker may be active or passive, and may be detectable using an optical detector. An example optical passive marker is a reflective sphere, or portion thereof, and an example active optical marker is an LED. Another example of a marker is a glyph, which may contain sufficient spatial and/or geometrical co-planar features for determining a three-dimensional position and orientation. For example, a glyph marker may include at least three corner features, where the three corner features define a plane.

As used herein, the term "marker plane" refers to the plane shared by one or more markers that are attached to a handheld implement, such that the tracking markers are suitable for determining a three-dimensional position and orientation of the handheld implement by the tracking system when the markers are secured to the handheld implement. The marker plane may be defined at an angle relative to the shaft of the medical instrument.

As used herein, the term "overhead tracking system" refers to a tracking system that is located above an object to be tracked. An overhead tracking system may be directly overhead, substantially overhead, or overhead and laterally displaced. In some embodiments, a line of sight vector between the object to be tracked (e.g. a trackable handheld implement) and the tracking system is oriented at an angle of at least 45 degrees relative to a horizontal plane.

FIG. 1 shows an illustration of an example of a surgical guidance system for tracking the intraoperative location and orientation of a medical instrument relative to patient anatomy during a spinal surgery. Patient 10 is shown in the prone position, with spine 15 exposed. The example system employs a combination of an optical tracking system and a structured light system.

The optical tracking subsystem is used to detect the position and orientation of medical instrument 40. In the example embodiment shown in FIG. 1(*a*), the optical tracking subsystem includes stereo cameras with integrated infrared lighting 25 and attachment of highly reflective markers 65 to medical instrument 40. Due to their high reflectivity to infrared light, markers 65 can be easily localized in each image of the two cameras 25. These image positions are used to calculate the 3D position of each marker 65 by geometrical triangulation. The triangulation process can be performed by first calculating the center of mass of each of the detected markers in both camera views of the stereo calibrated camera system. This yields a set of marker points in both camera views from which the disparity between corresponding points in both views can then be calculated. This disparity along with the x and y pixel locations of each marker in one of the camera views can then be transformed into a 3D spatial coordinate (in a relevant coordinate system) using a perspective transformation. If at least three markers 65 are rigidly attached to medical instrument 40, it is possible to compute its position and orientation (the six degrees of freedom—6-DOF). It is to be understood that in some embodiments, less than three markers may be employed for position and location tracking. For example, a single marker may be provided for position and location tracking, provided that the single marker includes sufficient spatial structure and/or content. An example of such a single marker is a glyph including co-planar spatial features such as corner or edge features.

In the example illustrations provided herein, markers 65 for the optical tracking system are shown as reflective spheres, which are commonly used for passive optical tracking. However, any other type of markers, or marker attributes, can be used depending on the used tracking system such as, but not limited to, active markers (i.e. LEDs, which do not require integration of additional lighting) and passive markers (e.g. glyphs, varying marker color, varying marker size, varying marker shape).

The structured light imaging subsystem shown in the example embodiment is used to generate topology datasets with sub-millimeter accuracy. It includes at least one illumination device 30 and at least one camera 35. The illumination device(s) 30 project temporally and/or spatially modulated light onto the surface to be imaged, while the camera(s) 35 capture images of the illuminated surface. This active illumination enables robust and efficient identification of pixel correspondences between calibrated camera-projector (a projector may be thought of as an inverse camera) or calibrated camera-camera system. The correspondence (disparity) data can then be transformed into real-space coordinate data in reference frame of the calibrated camera(s) 35 and/or projector(s) 30 by geometrical triangulation. During surgery, the structured light system is positioned such that 3D surface topology of the surgical site, such as bony surfaces of the exposed spine 15, is acquired and used to create a virtual representation of the exposed bone that is registered to pre-operative data (e.g. CT, MRI, US, PET, etc.) for continual surgical navigation.

In order to utilize the optical tracking data in conjunction with the structured light data, a calibration procedure can be employed to align the coordinate system of the optical tracking system to that of the structured light imaging system. If the relative position of the optical tracking system and the structured light imaging system is fixed, this calibration may be performed by obtaining the position of at-least 3 points for a calibration object from both systems, and align the points to obtain the calibration transform. Alternatively, the structured light imaging device may include fiducial markers, which may be tracked by the optical tracking system itself. In this configuration, the transformation between the coordinate system of the optical tracking system and structured light imaging system is continuously updated.

The structured light datasets can be registered to preoperative 3D image data (e.g. computer tomography (CT) or magnetic resonance tomography (MRT) data) on the processing device 45 using methods described in patent application (PCT/CA2011/050257, the Detailed Description and Figures of which are incorporated herein by reference). With the calibration between the structured light and the optical system, the tracked position of the medical instrument 40 is projected into the preoperative 3D image data. The result is presented to the surgeon as an overlay 85 on the registered 3D image data on a display 55 or other visualization devices.

As shown in FIG. 1(*a*), tracking unit 20 is positioned in an overhead orientation, above exposed spine 15. During a surgical procedure, medical instrument 40 may be oriented such that its shaft 70 is not aligned perpendicular to the view axis of tracking unit 20 (as shown in the Figure). In such a situation, which involves direct, substantially overhead viewing (e.g. into or above a surgical incision), the performance of the tracking system, and the ability to track medical instrument 40, may suffer when the markers 65 are arranged with a marker plane that is parallel to the axis 70 of the instrument shaft.

Figure 1B:
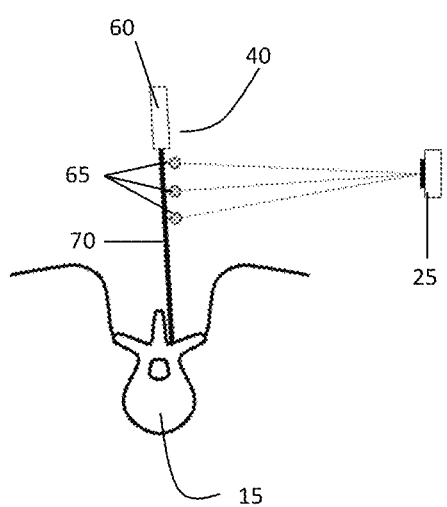
Figure 1C:
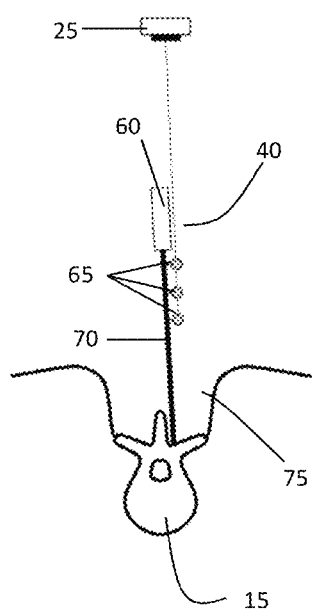

This conventional arrangement of markers is shown in FIGS. 1(b) and 1(c). FIG. 1(b) shows medical instrument 40 having handle 60 and shaft 70, with markers 65 attached in a plane that is substantially parallel to the axis of shaft 70. In FIG. 1(b), the optical tracking cameras 25 are oriented in a conventional side viewing geometry, which is suitable for assessing the position and orientation of medical instrument 30 over a wide range of angular orientations. Such an approach is commonly used in conventional tracking systems that do not require a direct view above and/or into the surgical incision 75.

As shown in FIG. 1(c), the conventional marker orientation is problematic when employed with the overhead, direct viewing system, (e.g. the overhead system shown in FIG. 1(a)). In the scenario illustrated in FIG. 1(c), in which cameras 25 are positioned above surgical incision 75, the conventional vertical plane marker arrangement leads to marker shadowing and/or occluding when medical instrument 40 is oriented near the vertical direction.

Figure 2A:
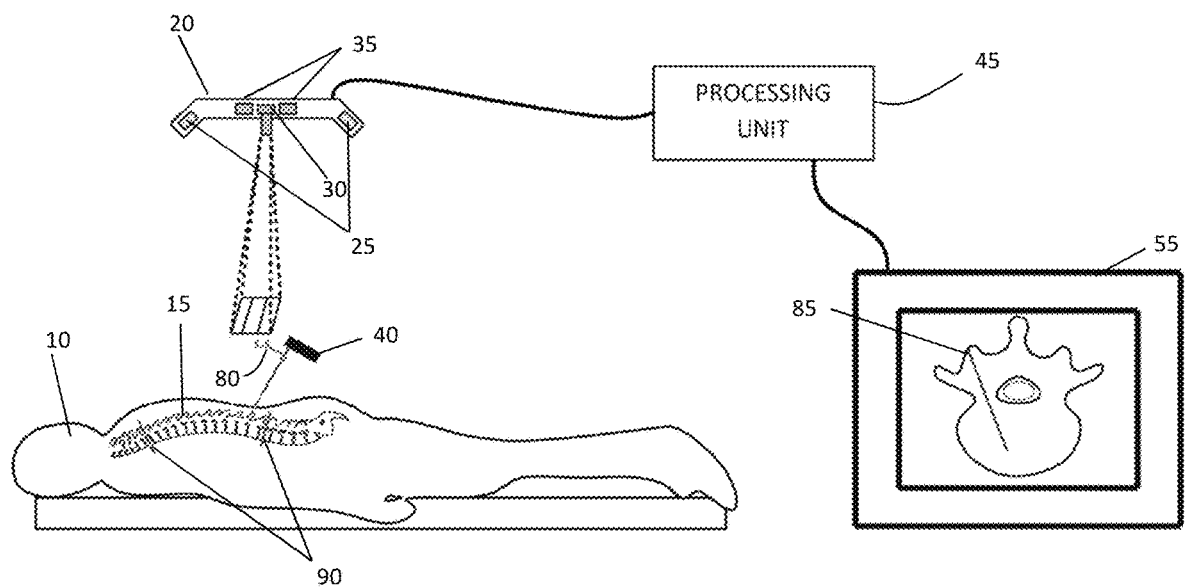
FIG. 2A provides an example surgical guidance system that includes an overhead integrated tracking system employing structured light surface detection for image registration and optical tracking of medical instruments and medical devices with marker attachments, where the markers are attached to the medical instrument in a plane that is not parallel to a longitudinal axis of the medical instrument, as further shown in FIG. 2B where full line of sight visibility of the markers is apparent.

FIG. 2(a) illustrates an embodiment of a surgical guidance system including tracking system 20, processing unit 45 (which is connectable to display 55), and medical instrument 40 including markers 65 that are oriented in a plane that is not parallel to the axis of medical instrument. Such an arrangement enables line of sight tracking of markers 65 over a wide range of angular orientations of medical instrument 40. Display 55 may be integrated with the system (for example, integrated with processing unit 45 in a single device), or may be an external device to which the processing unit 45 is externally connected. Furthermore, as described further below, the system need not necessarily include medical instruments 40 with markers 65 permanently attached thereto, and may additionally or alternatively include a marker 65 attachment assembly that is configured to be removably attachable to one or more medical instruments 40.

Figure 2B:
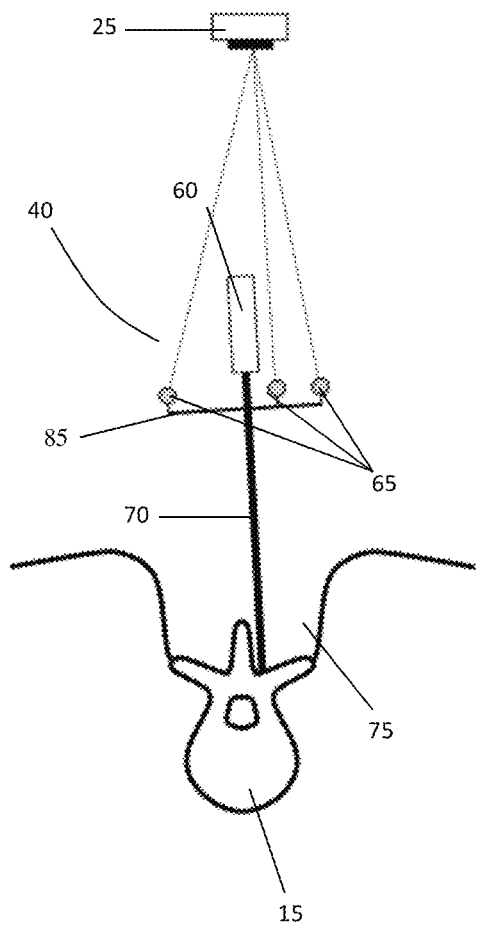

FIG. 2(b) provides an example embodiment showing relative positioning of the marker plane 85 and a longitudinal axis 70 of medical instrument 40. As can be seen in the Figure, markers 65 are provided in marker plane 85 that is not parallel to the longitudinal axis of medical instrument 40 (in the present example, the longitudinal axis is defined by shaft 70 of medical instrument 40). By orienting marker plane 85 such that it is an approximately horizontal plane for at least one potential intraoperative orientation of medical instrument 40, a direct line of sight may be maintained between cameras 25 and markers 65 over a wide variety of possible orientations of medical instrument 40.

Figure 3:
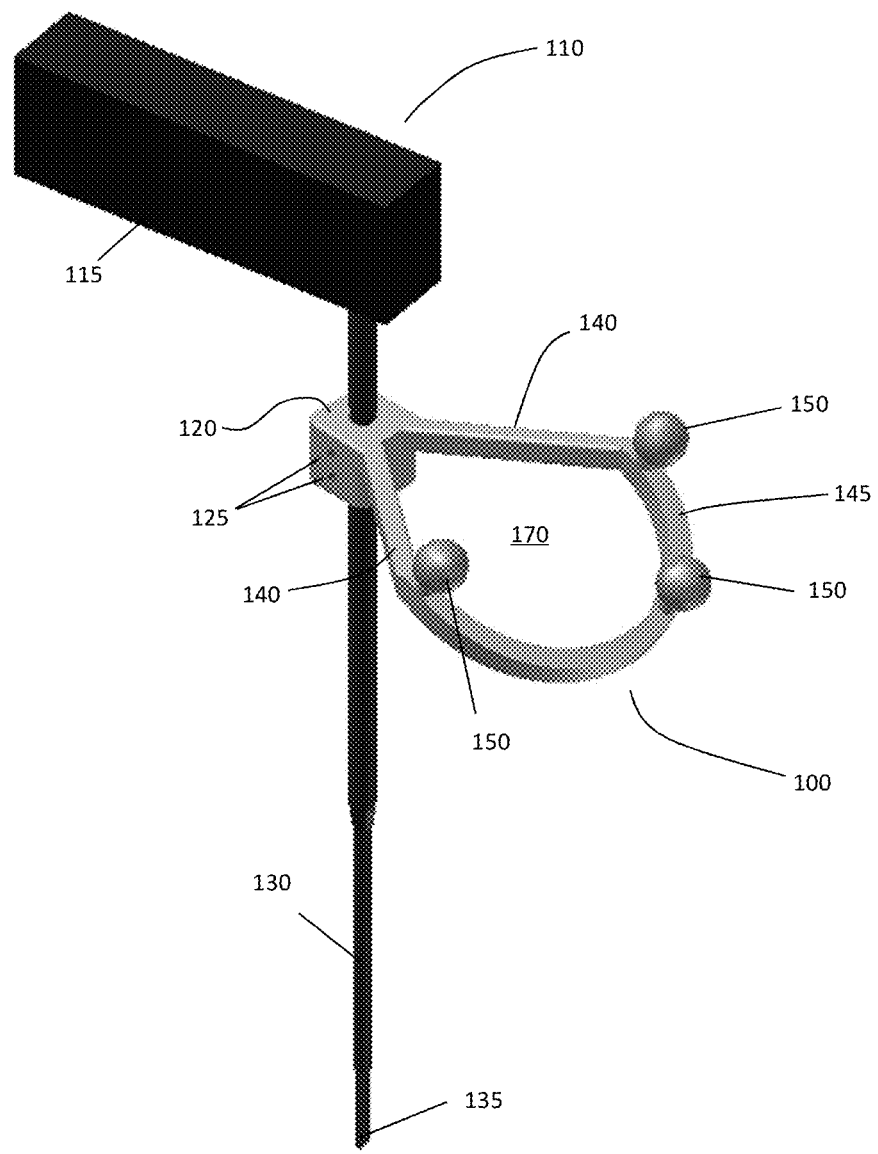
FIG. 3 provides an isometric view of an example marker assembly connected to a medical instrument.

FIG. 3 illustrates one example implementation of a removable marker assembly 100 according to an embodiment of the disclosure, where marker assembly 100 is shown as being removably secured to shaft 130 of medical instrument 110, below handle 115. Marker assembly 100 includes a support member (140, 145) for supporting tracking markers 150, which are aligned in a plane defined by distal arc 145. In this example, instrument shaft 130 is inserted through a hole in connector 120. Set screws 125 secure marker assembly 100 to shaft 130, preventing sliding and rotation of the marker assembly 100. Although connector 120 is shown provided as an integral portion marker assembly 100, connector 120 may be provided as a separate component that is slid, clamped, or otherwise secured to shaft 130, and may be separately interfaced or connected to marker assembly 100. Other example implementations of marker assembly 100 and connector 120 are described in more detail below.

The marker plane, as defined by distal arc 145, is angled relative to longitudinal axis 130, to enable line of sight detection of markers 150 by an overhead optical tracking system, over a wide range of overhead line-of-sight view angles. In the example embodiment shown in FIG. 4, the marker plane, as defined by distal arc 145, is shown angled relative to longitudinal axis 130 such that the marker plane is approximately horizontal when medical instrument 110 is oriented at an angle relative to the horizontal plane.

Figure 4:
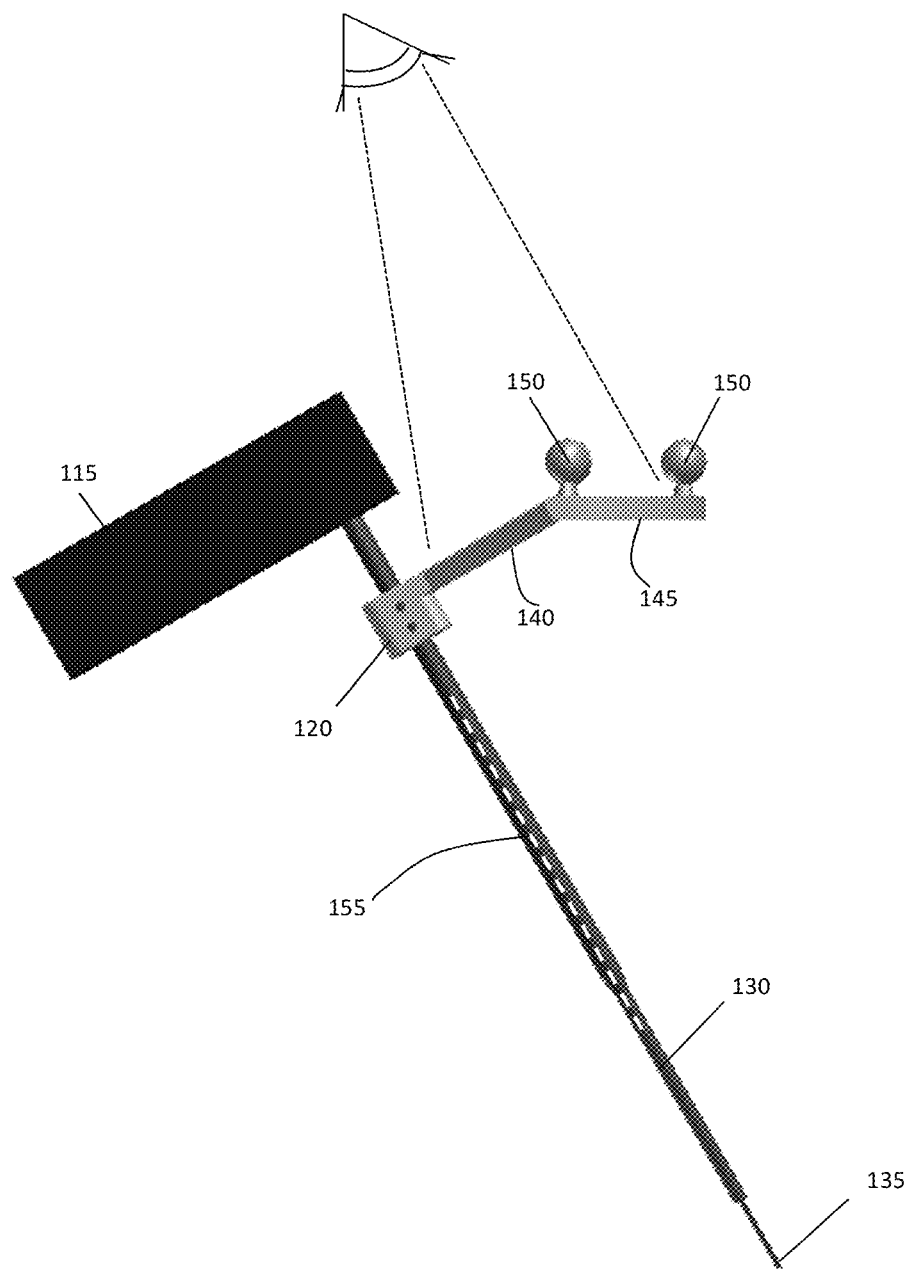
FIG. 4 is side view of the example marker assembly attached to the medical instrument, demonstrating the angle between the marker plane and the shaft of the medical instrument.

As shown in FIG. 4, distal arc 145 of marker assembly 100 is offset from longitudinal axis 130 by one or more proximal segments 140, which together with one or more distal segments 145, form a ring shaped structure. In some embodiments, proximal segments 140 may lie outside of the marker plane, as shown in the example provided in FIGS. 3 and 4. In some embodiments, proximal segments 140 extend from instrument shaft 130 along a direction that is approximately perpendicular to longitudinal axis 155 (or beyond perpendicular). This allows a user to grip shaft 130 beneath proximal segments 140, without proximal segments 140 contacting or pressing against the user's fingers. In other embodiments, one or more proximal segments extending from connector 120 may lie within the marker plane.

Figure 5A:
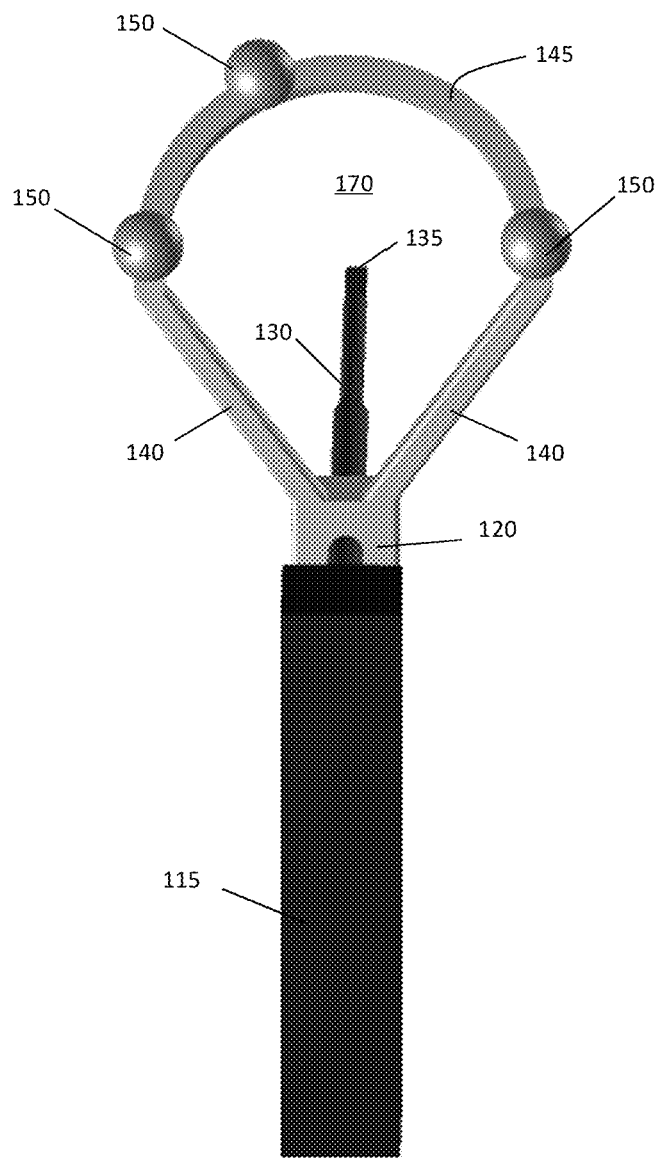
FIG. 5A provides a view of the example marker assembly attached to the medical instrument, where the view is directed downward along the shaft of the medical instrument, such that the distal tip of the medical instrument is visible.
Figure 5B:
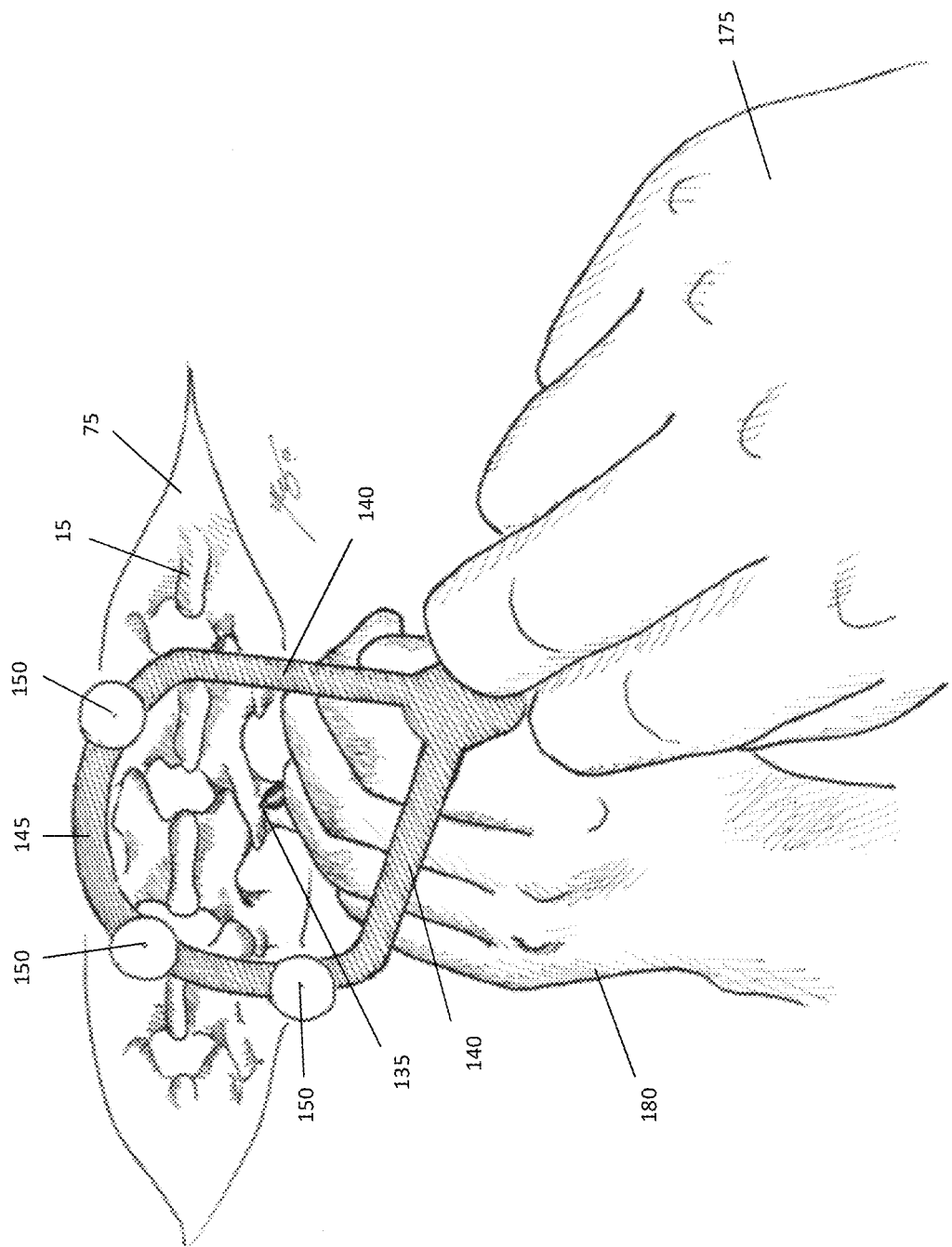
FIG. 5B shows an illustration of the surgeon's point of view of the optically tracked surgical instrument for medical implants.

The ring structure, with dual members 140, provides rigid structural integrity and resistant to external torque, thereby providing a resilient assembly. Furthermore, the ring structure defines a hole 170 (shown in FIGS. 3 and 5) through which a surgeon or other user may look when operating with medical instrument 110 (as shown in FIG. 4). As can be seen in FIG. 5(a), which illustrates the view from the perspective of the surgeon, the ring shape allows the surgeon a clear view on the distal tip 135 of the shaft 130 during the normal use of the medical instrument. The surgeon is therefore able to visibly check the incision or touching point of the medical instrument. This is illustrated in a sketch of the surgeon's view through the marker attachment in FIG. 5(b). The surgeon's dominant hand for implant insertion (175) holds the handle of the tool while the non-dominant hand (180) resting on the edge of the surgical incision 75 aligns the tool shaft. A clear view on the distal tip 135 and the exposed spine 15 is obtained for the surgeon.

The angle between the instrument longitudinal axis 155 in FIG. 4 and the marker plane can vary for different attachment designs depending on the type of medical instrument 110, and the range of insert angles of the instrument into the body. In one embodiment, the relative angle between the longitudinal axis and the marker plane may be determined as follows. A range of angles corresponding to typical use of the medical instrument 110 is first determined. The relative angle between the longitudinal axis 155 and the marker plane is then selected such that when the medical instrument 110 is oriented at the midpoint of this angular range, the marker plane is approximately orthogonal to the expected view axis of the overhead tracking system. In embodiments in which the view axis is approximately in the vertical direction (i.e. direct overhead viewing), then the marker plane is selected to be approximately horizontal.

For example, the angular range for inserting pedicle screws during spinal surgery depends on the treatment area/level and is patient and disease specific since various diseases induce different kinds of spinal deformations. Surgical operation ergonomics dictate that typical surgical incisions occur directly in front of the principle surgeon, with both hands in a comfortable position. The operating room light and other assistive devices (e.g., tracking system, LCD display, etc.) are typically maneuvered, by the surgeon's upper extremity, in an abducted and externally rotated position, along an arc that is approximately 120 cm to 150 cm in radius from the surgical incision. The surgeon's operative view has a surgical axis defined by his/her nasion and the center of the surgical incision. Accounting for potential obstruction by the surgeon's head, the optical axis (for operating room light or optical tracking system) can be located approximately 30° off the surgical axis (see 90 in FIG. 2(*a*)). Given this geometrical consideration, coupled with operative experience, a range from approximately 50° to 70° for the relative angle between the longitudinal axis and the marker plane provides optimal tracking of the instruments used during pedicle screw placements.

It is to be understood that this angular range is provided as an example, and that for other types of medical instruments, the suitable angular range may differ. The suitable angle range for a given medical instrument may be determined by considering the typical orientations of the medical instrument during use.

In the marker assembly shown in FIG. 4, the relative angle between the longitudinal axis 155 of the medical instrument 110 and the marker plane is fixed. Further embodiments of the marker assembly allow the setting of various angles by the user. The following embodiments provide some example implementations in which pivotable, tiltable, hinged and/or rotatable mechanisms are provided for varying the angular orientation of market assembly 100.

Figure 6A:
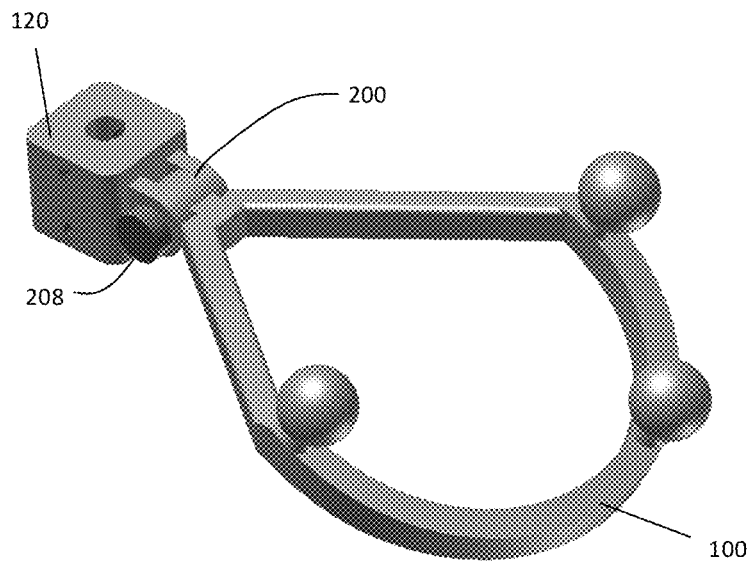
FIG. 6A shows an example marker assembly based on a hinge joint, which allows the user to select any arbitrary angle between the connector and the marker arrangement, and FIG. 6B a detailed view of the individual components of the hinge joint.
Figure 6B:
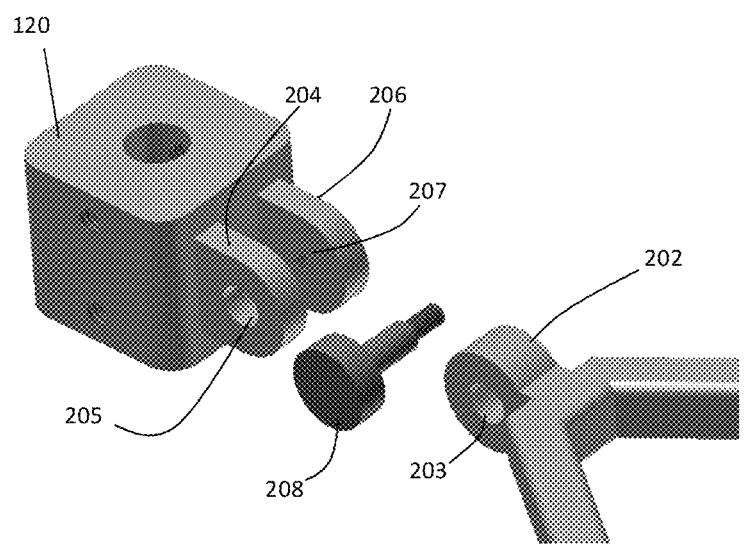
Figure 7:
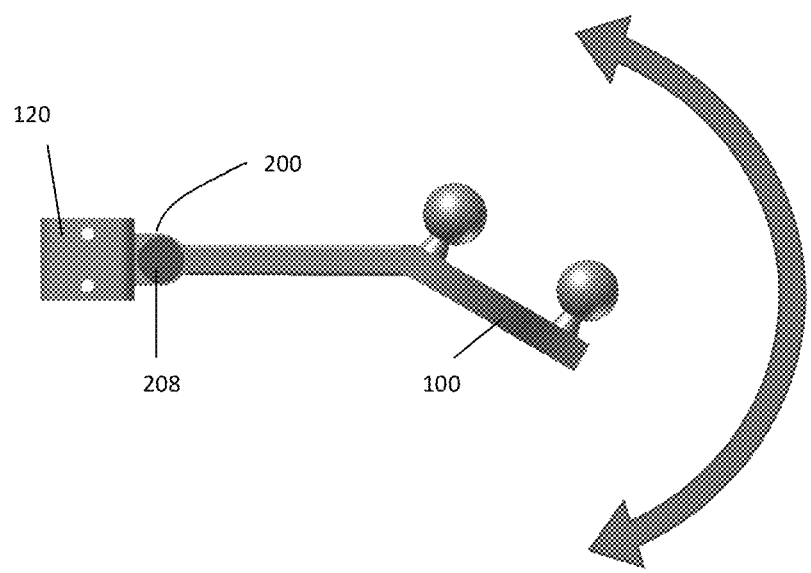
FIG. 7 illustrates the possible angle settings using the hinge joint between the connector and the marker arrangement as shown in FIGS. 6A-6B.

In one embodiment shown in FIGS. 6(*a*) and (*b*), a hinge joint 200 is employed to vary the angular orientation of marker assembly 100. Hinge joint 200 includes pivot member 202, which is integral with marker assembly 100, and which is received between support members 204 and 206, which are integral to connector 120. Fixation screw 208 is placed through hole 205 in support member 204 and hole 203 in pivot member 202, and is received in threaded hole 207 in support member 206, such that support members 204 and 206 clamp pivot member 202 in place at a selected angle. This allows the user to select an arbitrary angle as shown in FIG. 7. After fixing the angle with the fixation screw 208, the tool may be calibrated before tracking.

Figure 8A:
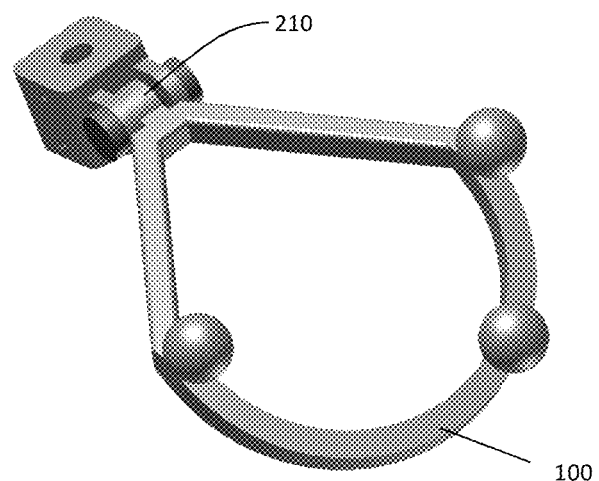
FIG. 8A shows an example marker assembly based on a hinge joint with notches and a spring which allows the user to select an angle from predefined angle settings between the connector and the marker arrangement, and FIG. 8B a detailed view of the individual components of the hinge joint.
Figure 8B:
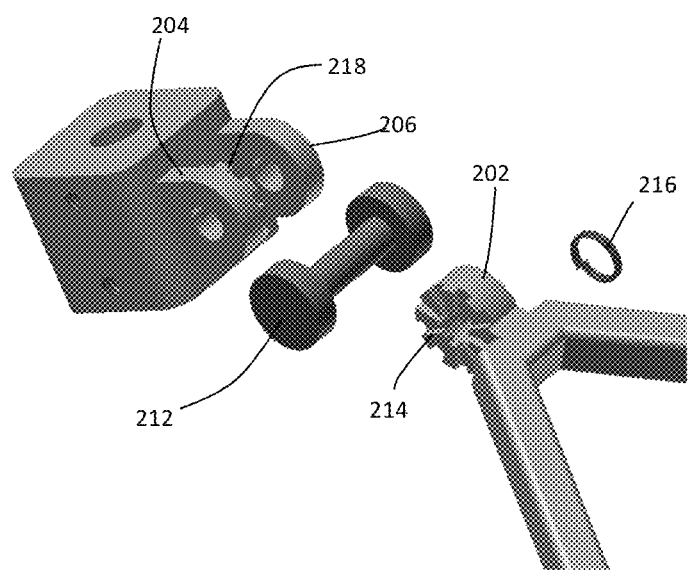

Fixation screw 208 provides but one example of a locking mechanism that may be employed to lock the angle of the pivotable marker assembly 100. For example, in another embodiment, shown in FIG. 8, provides a hinge joint 210 that is pivotable among a series of pre-selected angular orientations. Pivot member 202 is supported between support members 204 and 206 on support bar 212. Pivot member 202, which includes notch structures 214, is biased by spring 216 towards corresponding notch structures 218 on support member 204. The user can choose between certain pre-defined angle settings.

Figure 9A:
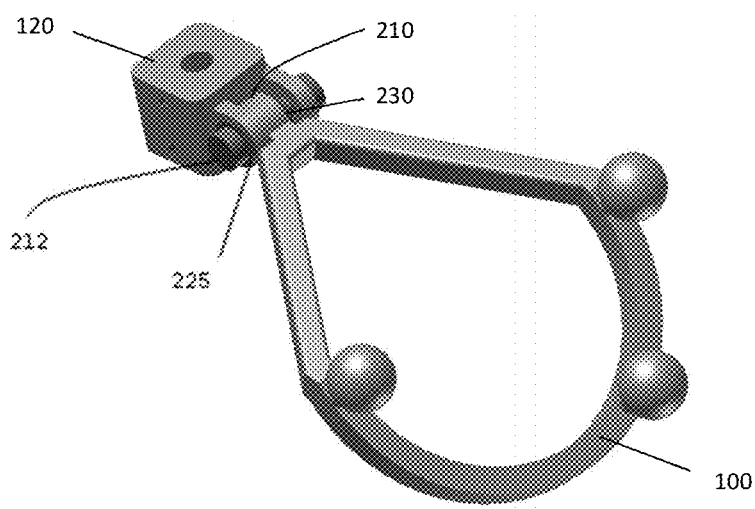
FIGS. 9A-B show the example marker assembly from FIGS. 8A-8B, where the magnetic clamp mechanism is used instead of a spring.
Figure 9B:
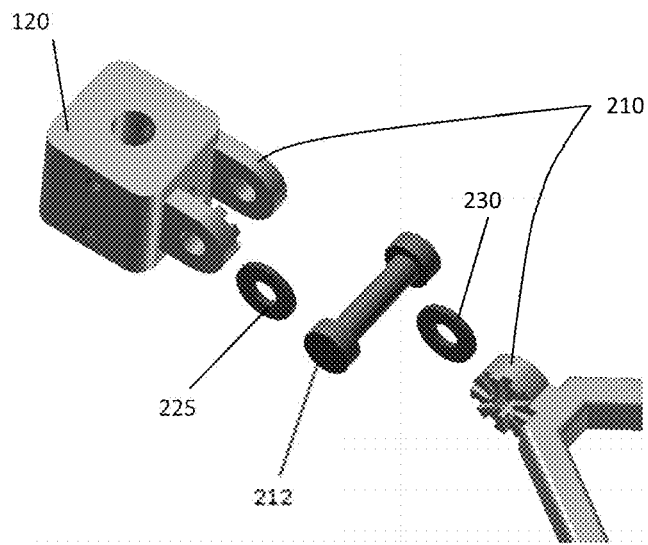

In another example embodiment shown in FIG. 9, two magnets 225 and 230 are employed to provide a biasing mechanism for fixing marker assembly 100 at the selected angle. As a further modification of this embodiment, one of the two magnets 225 or 230 could be replaced by a magnetizable material.

Figure 10A:
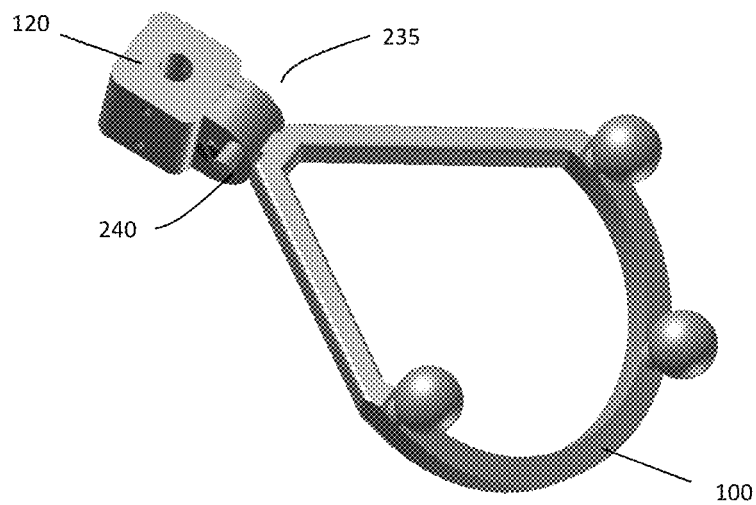
FIG. 10A shows an example marker assembly based on a hinge joint with a pin fixation which allows the user to select an angle from a set of predefined angles between the connector and the marker arrangement, and FIG. 10B a detailed view of the individual components of the hinge joint.
Figure 10B:
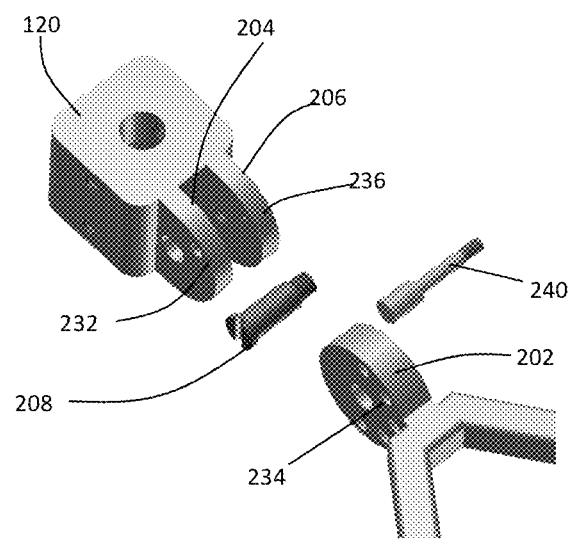

In another embodiment shown in FIG. 10, a hinge joint 230 includes locking pin 240 for fixation of pivotable marker assembly 100 in one of several possible angular orientations. A shown in FIG. 10(*b*), fixation screw 210 is employed to support pivot member 202 between support members 204 and 206. Unlike the embodiment shown in FIG. 6, however, pivot member is held in a fixed orientation by the placement of locking pin 240 with holes 232, 234 and 236 in support member 204, pivot member 202, and support member 206, respectively. Pivot member 202 includes a plurality of such holes, such that the angular orientation of marker assembly 100 may be varied without detaching marker assembly 100 from connector 120.

Figure 11A:
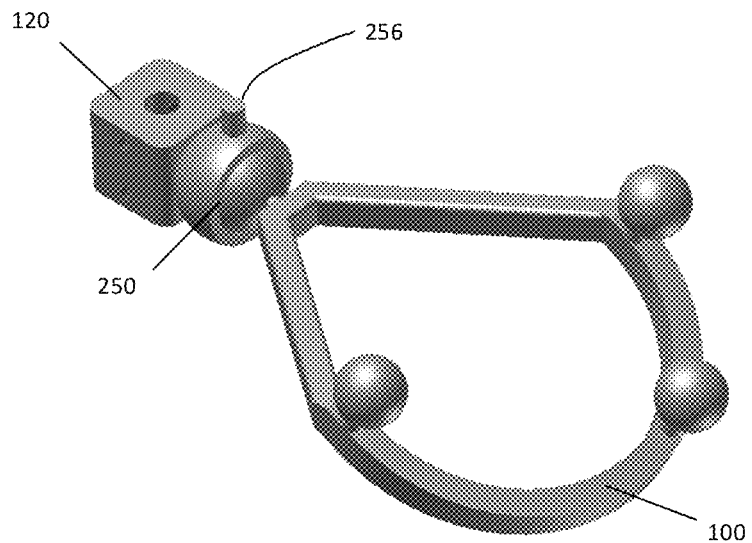
FIG. 11A shows an example marker assembly based on a ball joint which allows the user to select any angle between the longitudinal axis of the medical instrument and the marker arrangement, and FIG. 11B a detailed view of the individual components of the ball joint.
Figure 11B:
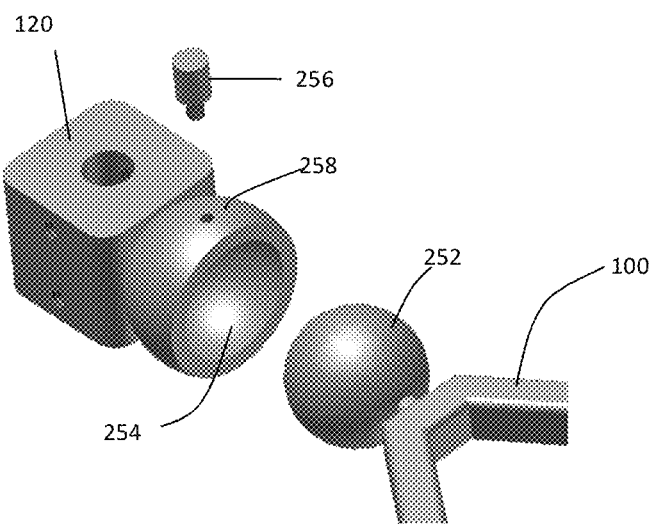

In the embodiment shown in FIG. 11, a ball joint 250 is employed to pivotally secure marker arrangement 100 to connector 120. Ball joint 250 includes convex hemispherical member 252, which is attached to, or integral with, marker assembly 100, and which is received in concave hemispherical portion 252, that is attached to, or integral with, connector 120. A fixation screw 256 is received in threaded hole 258 within concave hemispherical portion 254 for securing ball joint 250 in a given angular orientation. Ball joint 250 allows the user to select an arbitrary angle between the longitudinal axis 155 of the medical instrument 110 and the marker plane.

When the aforementioned embodiments with a variable angular orientation of marker assembly 100 are attached to a medical instrument and employed with a guidance system, it will generally be necessary to either calibrate the medical instrument or to select the calibration result from a list of previously performed calibrations prior to initiating tool tracking. Common methods of performing calibration include, but is not limited to inserting the tip of the tool 135 into multiple landmarks of a calibration block with known (calibrated) geometry, and pivot calibration, where the tool tip 135 is fixed in space, while the axis of the tool 155 is pivoted about the tip 135. Both these methods allow the tip 135 and axis 155 of the tool to be defined in terms of the markers 150. However, in some of the aforementioned embodiments in which a finite number of fixed angular orientations are available, it may possible to calibrate one of the many selectable angular orientations, and to employ the known angular relationship among the different angular orientations to calibrate any of the other angular orientations.

The ring shape of marker assembly 100, shown in FIG. 3 with a round arc, is but one non-limiting example implementation of many possible shapes for marker assembly 100. FIG. 12 illustrates additional non-limiting example shapes and configurations with an open or closed ring shape. For example, FIG. 12(*a*) shows a schematic of the round arc-shaped example marker assembly extending from connector 120. Other design examples are based on (b) a full circle shape, (c) a rectangular shape, (d) a triangular shape, and (e) a hexagonal polygonal shape. In other embodiments, marker assembly 100 may include an open gap, as shown in FIG. 12(*f*), and/or have arms on each side with dissimilar shapes and/or lengths, as shown in FIG. 12(*g*).

Embodiments of the marker assembly may be configured for attachment to different types of medical tools. Two example types of medical instruments with longitudinal shafts are shown in FIG. 13, in which the illustrated medical instruments differ according to their handling by the surgeon. FIG. 13(*a*) shows a first example instrument type, such as an awl or a pedicle finder 110, which are typically rotated, relative to the longitudinal axis of shaft 130, clockwise or counterclockwise 300 by less than approximately 180°. For such instruments 110, a fixed connection may be made between the instrument shaft and the marker assembly 100. As a consequence, the marker assembly 100 is rotated in unison with the medical instruments 110 around the shaft 130. If the rotation angle does not exceed 180°, the surgeon does not interrupt the ability of the optical tracking system to maintain line of sight visibility, and therefore, the tracking ability to track the instrument is maintained.

Figure 14A:
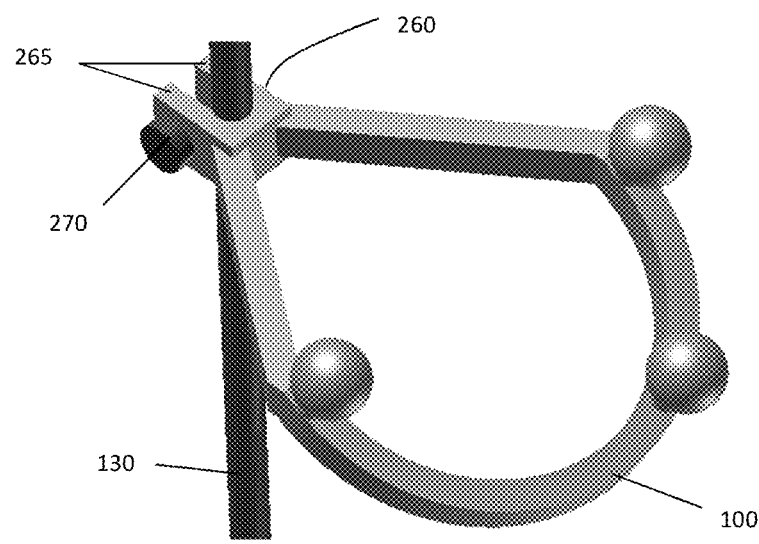
FIG. 14A shows an example marker assembly with a clamp that has two claws, which allows a fixed connection between the shaft of the medical instrument and the marker arrangement, and FIG. 14B a detailed view of the individual components of the clamping mechanism.
Figure 14B:
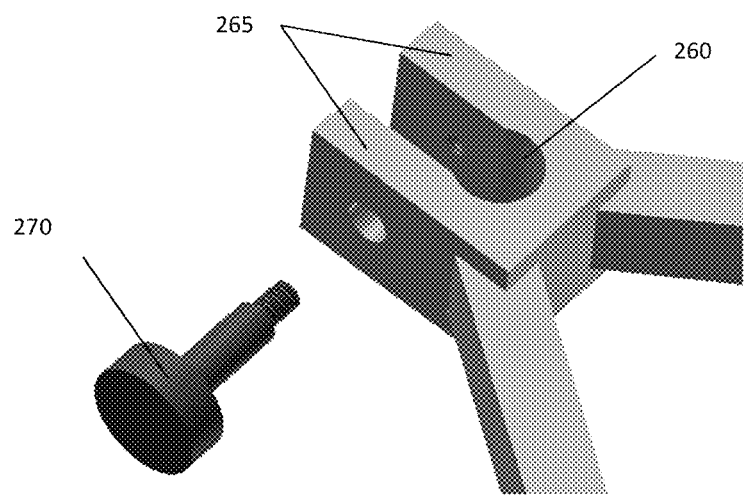

One example of a fixed connection is the insertion of the instrument shaft 130 through a hole in a connector block 120 and fixation of the arrangement with set-screws 125, such as in FIG. 3. Another fixed connector with a marker arrangement 100 is a clamp 260 with two claws 265, which attaches to the longitudinal shaft 130 of the medical instrument 110 as shown in FIG. 14. An additional fixation screw 270 could be used to squeeze the two claws 265 and thereby secure the connector tighter onto the instrument shaft 130.

Figure 15C:
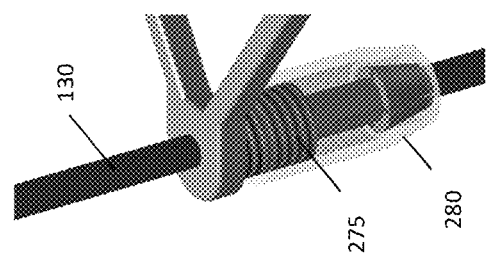
FIGS. 15A-15C show the example marker assembly with a fixed connection between the shaft of the medical instrument and the marker arrangement based on a collet chuck adaptor, showing FIG. 15A the marker arrangement with the spring collet and the nose piece, FIG. 15B the marker assembly attached to the shaft of a medical instrument, and FIG. 15C a semi-transparent view of the attachment.
Figure 15B:
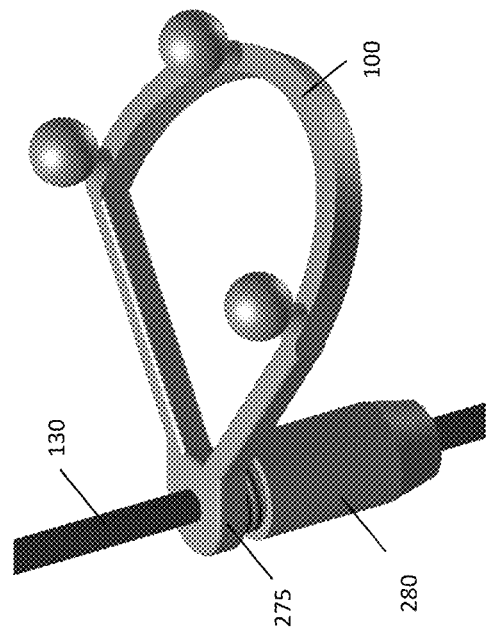
Figure 15A:
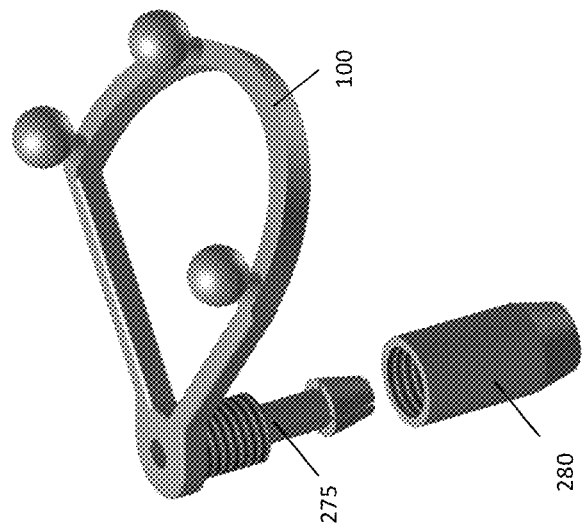

Another fixed connector with a marker arrangement 100 is a collet chuck adaptor as shown in FIG. 15. A spring collet 275 is fixed to, or integral with, marker assembly 100. After inserting shaft 130 of medical instrument 110, nose piece 280 fastens the spring collet 275, and thus marker assembly 100, to shaft 130.

Figures 13A, 13B:
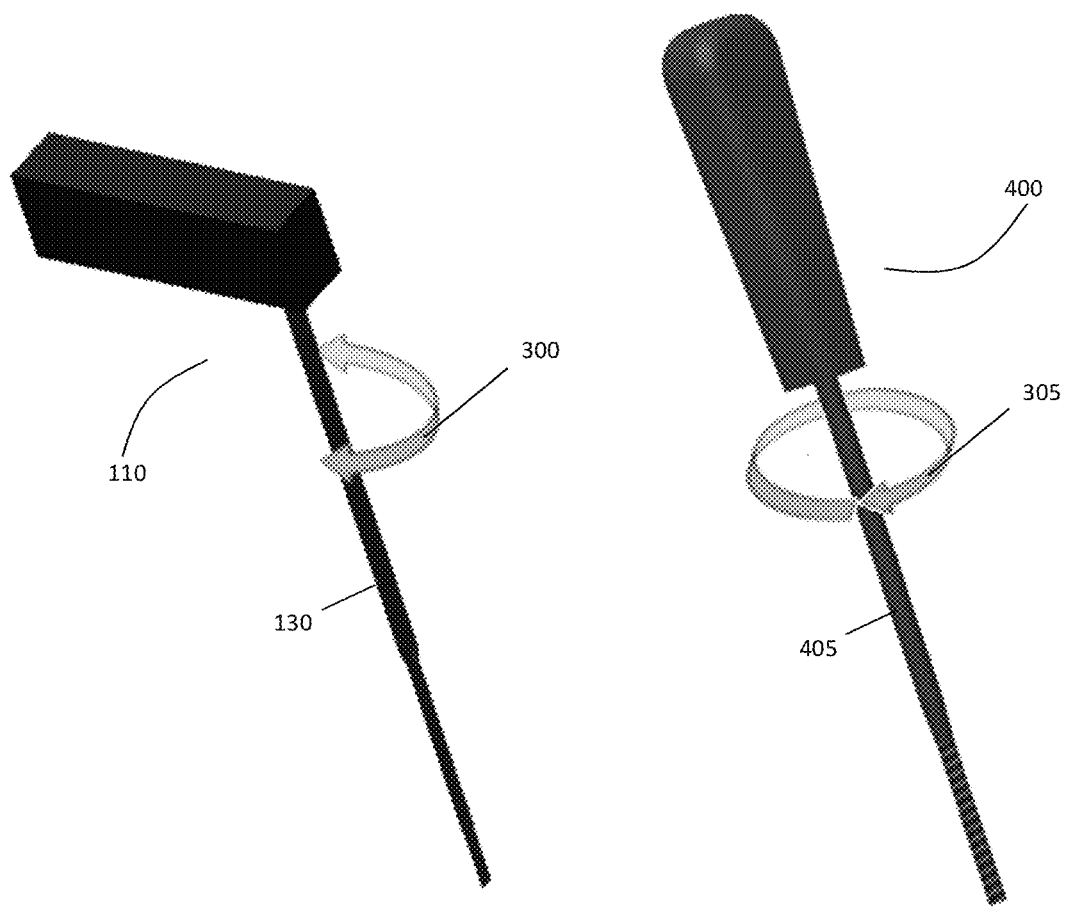
FIGS. 13A-13B illustrates the two example types of medical instruments that differ by their handling by the surgeon, showing FIG. 13A an instrument that is twisted clockwise or counterclockwise by a small angle around its shaft, and FIG. 13B an instrument that is fully rotated several times.

A second type of medical instrument is shown in FIG. 13(b), which includes, for example, screwdrivers and taps 400. These instruments are normally rotated several times in the same direction 305 around the longitudinal axis of the instrument shaft 405. For such instruments, the marker assembly may include a connection that allows a free rotation of the instrument shaft relative to marker assembly 100. For example, as described further below, the marker assembly and connector may include a portion that is clasped by the surgeon with one hand, providing support and enabling the surgeon to maintain the visibility of the marker assembly by the tracking system. This ensures that the surgeon does not block the line of sight of the tracking system on the tracking markers during rotation of the medical instrument 400. Accordingly, unintended blocking of line of sight on the markers by the arms of the surgeon is avoided, maintaining the ability to track the medical instrument 400 during use.

One example embodiment of such a connector is shown in FIG. 16(a), which includes a pivotable marker assembly 410 with an inner hole that is sufficiently large to accommodate the outer diameter of shaft 405 of medical instrument 400. Stopper rings 415 and 425 (optionally secured with fasteners such as set-screws), or other structures along the instrument shaft, fix or limit the relative position of the pivotable marker assembly 410 along instrument shaft 405. As illustrated in FIG. 16(b), during surgical use, the surgeon clasps the elongate cylindrical portion 420 of pivotable marker assembly 410 with one hand, while the other hand can be used to rotate medical tool 400 by grasping handle 430.

Figure 17B:
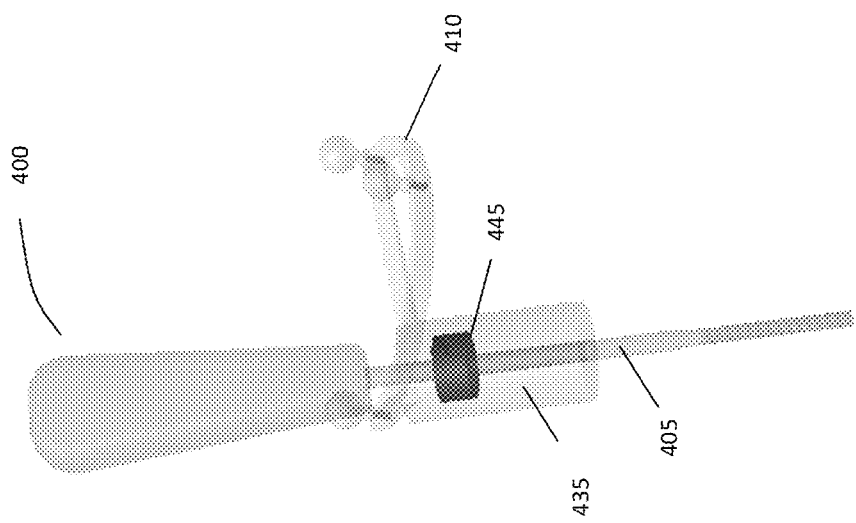
FIG. 17A shows the example marker assembly attached to a rotatable medical instrument, where only one stopper ring is used and FIG. 17B a semi-transparent view to show the position of the stopper ring inside the handle.
Figure 17A:
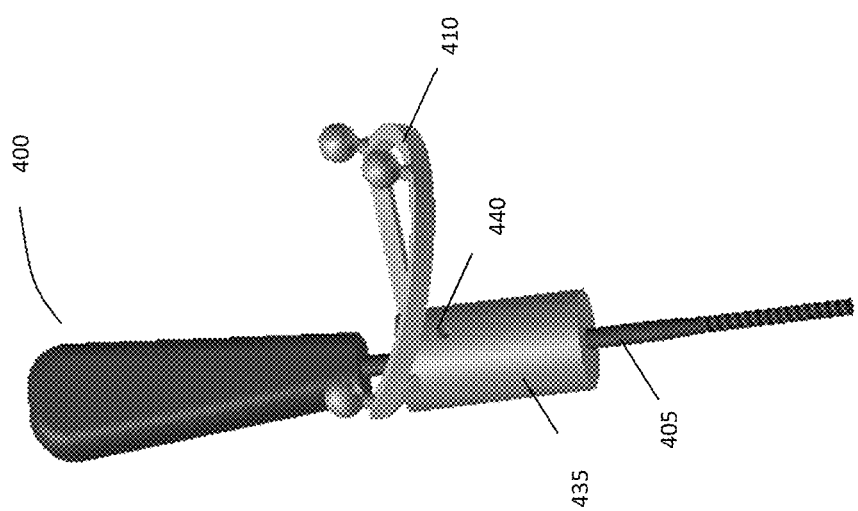
Figure 18A:
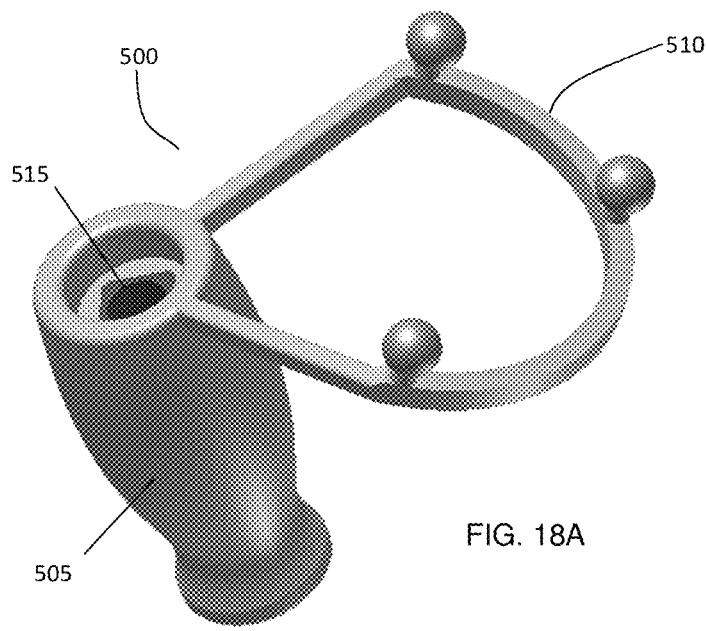
FIGS. 18A-18C show components of an example embodiment of a marker assembly that allows the marker assembly to be removably attached to different medical instruments, showing FIG. 18A the marker assembly, FIG. 18B the connection adapter which is attached to each tracked medical instrument, and FIG. 18C a calibration tool to ensure that the same distance between the connection adapter and the tip of the medical instrument is obtained.
Figure 18B:
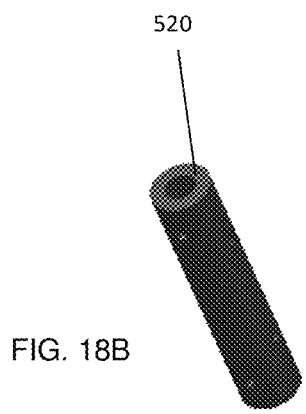
Figure 18C:
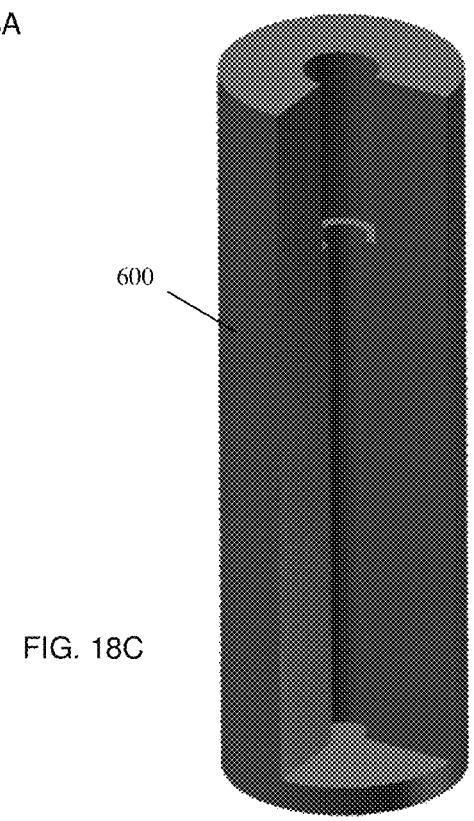

It should be recognized that variations and modifications of the mechanism for connection between the marker assembly 410 and shaft 405 of the medical instrument 400 may be implemented. For example, one ring 445 can be integrated into the pivotable cylindrical portion 435 of the marker assembly 410 as shown in FIG. 17. The ring 445 is secured with fasteners such as set-screws (using the hole 440) and fix of the pivotable marker assembly 410 along shaft 405 of the medical instrument 400.

Many commercially available tracking systems are compatible with limited arrangements of markers on tracking attachments. For example, optical tracking systems that employ passive spherical optical markers typically require a minimal distance between markers and specific variations in the distances between marker pairs in order to track multiple instruments. As a consequence, the relative spacing of the markers becomes larger with the number of tracked instruments when each instrument is tracked with an individual marker arrangement. Unfortunately, larger marker attachments make it more difficult and less convenient for the surgeon to handle the medical instruments.

In one embodiment, a connection adapter is attached to, or provided as part of, the medical instrument itself (for example, permanently affixed to the shaft, or formed as a monolithic component of the shaft), such that the connection adapter is configured to mate with, or otherwise connect to, the removably attachable marker assembly. Multiple connection adapters, each having a common outer cross-section (cross-sectional profile), may be provided, for attachment to multiple medical instruments. Such an embodiment enables one marker assembly to be used for a plurality of different medical instruments, even if the shaft diameter, or shaft length, differs among the medical instruments.

Accordingly, in one example embodiment, which may be employed to reduce the number of marker assemblies needed for tracking of multiple medical instruments, a connection adaptor is integrated with, or attached to, one or more medical instruments to be tracked, where the connector allows the coupling and removal of one marker assembly to multiple medical instruments. In some embodiments, the coupling mechanism may support the repeated coupling and decoupling of the marker assembly to multiple medical instruments without the need for recalibration.

FIGS. 18-21 illustrate an example embodiment of a removably attachable marker assembly in which magnetic clamping is employed to secure an attachment assembly to a connection adapted attached to the shaft of a medical instrument. A first component is marker assembly 500, which includes handle 505 and marker support 510. During use, handle 505 is held by the surgeon with one hand, as described in the previous section. Handle 505 includes bore 515 extending below the top of the device.

Connection adapter 520 is a cylinder formed, at least in part, from a magnetic material, such as a diamagnetic, paramagnetic, or ferromagnetic material. In one example embodiment, connection adapter 520 may be formed from magnetic steel. Connection adapter 520 is placed around and secured to the shaft of the medical instrument. Connection adapter 520 may then be rotatably received within bore 515 within handle 505 in order to indirectly couple marker assembly 510 to the medical instrument. As further described below, an integrated magnet within handle 505 secures magnetic connection adapter 520 via an attractive magnetic force, thereby removably attaching marker assembly 510 to the medical instrument. An additional calibration tool 600, described in further detail in FIG. 22, allows the positioning of connection adapter 520 at a well-defined distance along the shaft from the tip of the medical instrument, allowing exchanging of marker assembly 500 among multiple pre-calibrated medical instruments without the need for intraoperative re-calibration.

FIG. 19 illustrates an example implementation of the internal components of marker assembly 500 (shown in from an external perspective in FIG. 19(a)). In FIG. 19(b), an exploded view of the internal assembly is provided, showing internal sleeve 525, which is also formed from a magnetic material and includes providing inner bore 515 for receiving connection adaptor 520. Ring magnet 530 is supported below counter piece 525 above end cap 535. Ring magnet 530 has an outside-diameter larger than the diameter of bore 515, and an inside diameter that is larger than the diameter of the largest shaft associated with the medical instruments to which the marker assembly is to be removably attached. A semi-transparent view through assembled marker assembly 500 is illustrated in FIG. 19(c), showing the position of internal sleeve 525, ring magnet 530 and fixation end cap 535 inside handle 505.

Figure 20A:
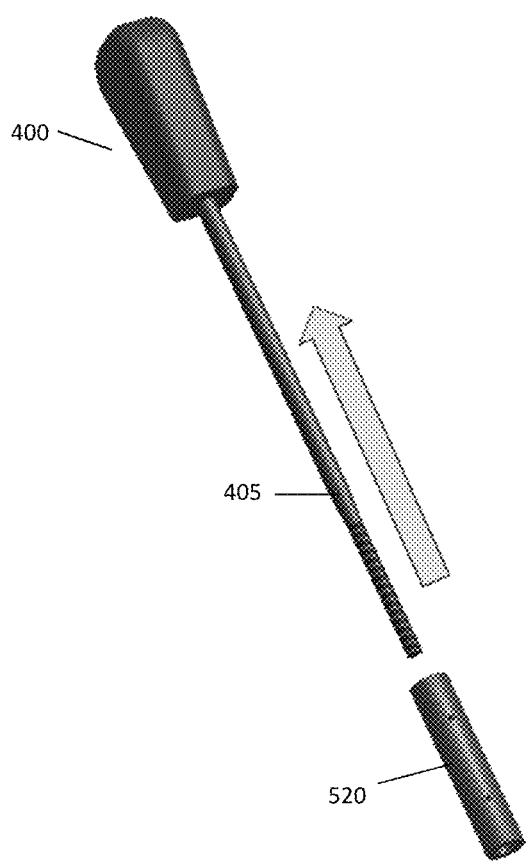
FIGS. 20A-20B illustrate the placement of the connection adapter onto the medical instrument.
Figure 20B:
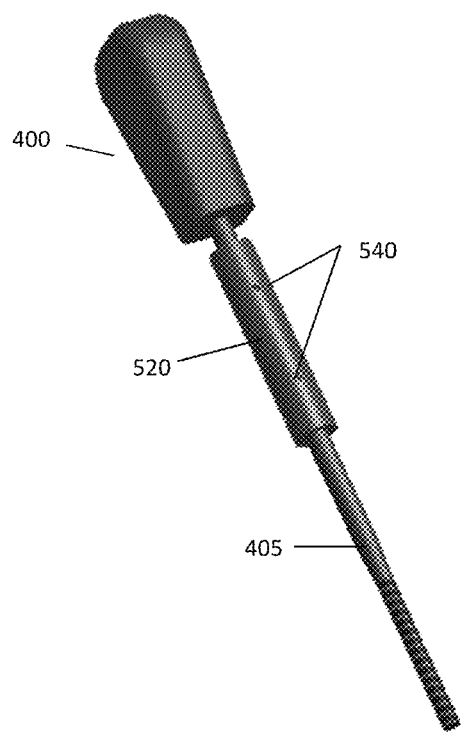

The operation of rotatable marker assembly 500 is described as follows. For each medical instrument 400 in a set of instruments to be tracked during surgery, a connection adapter 520 is provided and secured to the instrument shaft (as shown in FIG. 20). Each connection adapter 520 has an inside bore configured to receive the shaft 405 of its corresponding medical instrument 400. As shown in FIG. 20(a), the connection adapter 520 is slid along the shaft 405 of the medical instrument 400. Connection adapter 520 is then fixed with set-screws 540 at the desired position on the instrument shaft 405 as seen in FIG. 20(b).

Figures 21A, 21B:
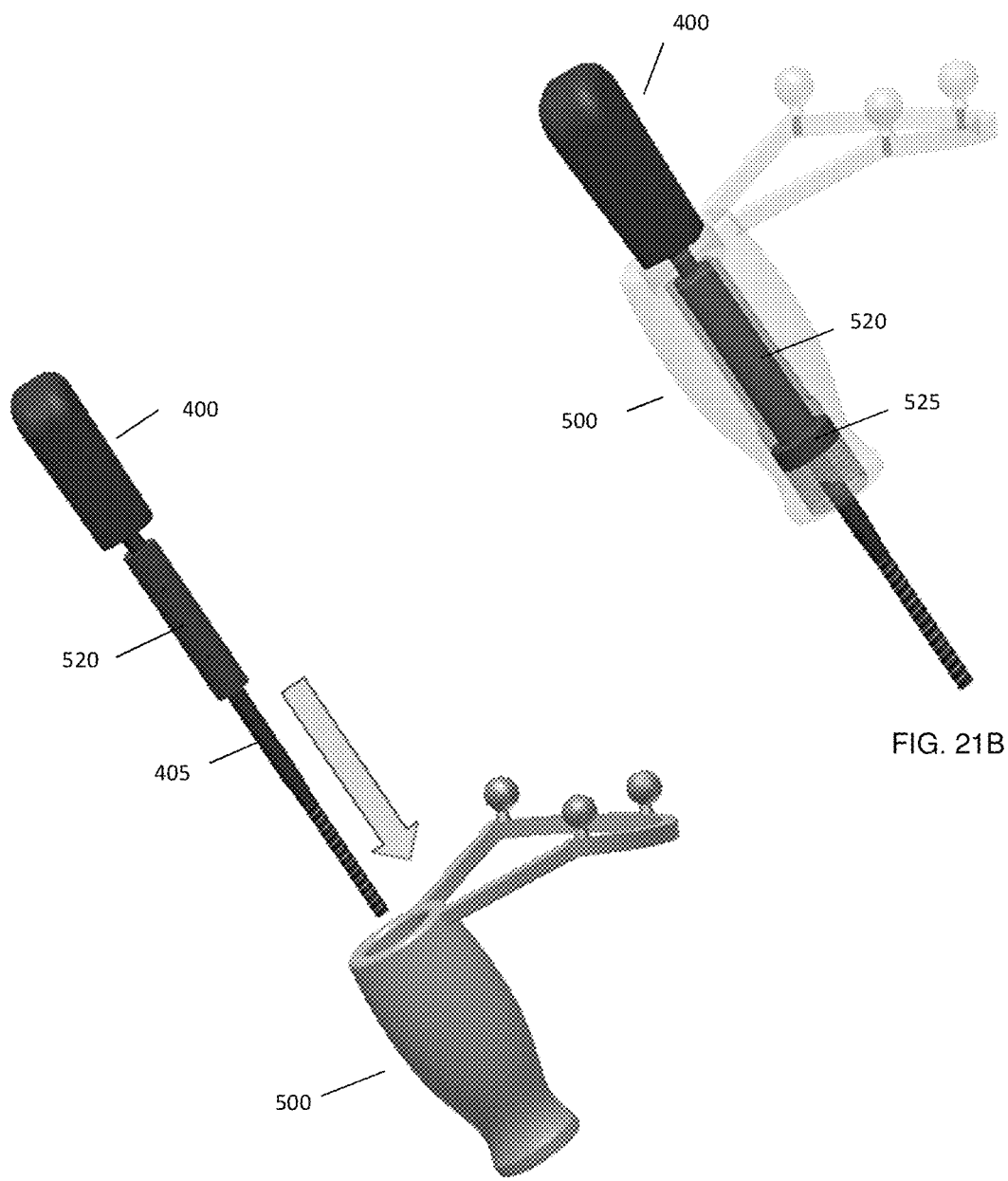
FIGS. 21A-21B illustrate the clamping of the marker assembly onto the medical instrument.

Marker assembly 500 is then slid over connection adapter 520 and detachably secured in place, as shown in FIGS. 21(a) and 12(b). To clamp medical instrument 400 to marker assembly 500, the instrument shaft 405 and connection adapter 520 are inserted through the bore 515 of within internal sleeve 525. As shown in the semi-transparent view of FIG. 21(b), connection adapter 520 is directly clamped to ring magnet 525 inside marker assembly 500. If the position of connection adapter 520 is not changed, the relationship between marker assembly 500 and the medical instrument 400 is well-defined and reproducible as required for the tracking of the instrument. Marker assembly 500 thereby enables the tracking of the trajectory of the instrument shaft 405 via an overhead optical tracking system.

This approach is efficient to track medical instrument 400 after the calibration, using the calibration procedures of the specific tracking system. The approach can also be used to track the trajectory of multiple instruments using the same marker attachment.

However, if tracking of the trajectory and the tip multiple medical instruments is desired, the position of connection adapter 500 on the shaft 405 of each medical instrument 400 may be calibrated such that the distance between the connection adapter 520 and the tip of each medical instrument is substantially equal.

This may be achieved, in one example embodiment, using a calibration tool. For example, calibration tool 600, shown in FIG. 18(c), may be employed to connect the connection adapter 520 to the shaft 405 of the medical instrument 400, as demonstrated in FIG. 22. Connection adapter 520 is initially placed into the top hole 605 of calibration tool 600, and is inserted until its motion is impeded by stop 610, which is a location at which the inner diameter of calibration tool 600 decreases from the outer diameter of connection adapter 520 to a smaller diameter, which is larger than the diameter of the largest shaft used in a medical instrument set. Accordingly, after the connection adapter 520 is fully slid into the hole 605, it is located with a well-defined distance relative to the bottom 615 of calibration tool 600.

Shaft 405 of the medical instrument 400 is then inserted though the bore 545 in connection adapter 520, until the tip of the instrument shaft 405 encounters the bottom 615 of calibration tool 600. Afterwards, as shown in FIG. 22(c), set-screws 540 of connection adapter 520 are tightened, thereby securing connection adapter 520 to the medical tool 400. Using this approach ensures that connection adapter 520 is always positioned in the same distance from the shaft tip of the medical instrument 400, and therefore, a re-calibration of the medical instrument 400 is not necessary.

The aforementioned devices and methods allow tracking of multiple medical instruments with one attachment (or a plurality of attachments, if so desired), provided that connection adapter 520 of each instrument is initially placed at a pre-calibrated location. This may be achieved, for example, using calibration tool 600 and following the procedure as shown in FIG. 21. In addition, no re-calibration is necessary for future uses of the tool (e.g. for the next surgery), provided that the connection adapters are either left on the medical instruments or removed and replaced using the calibration tool.

Figure 23B:
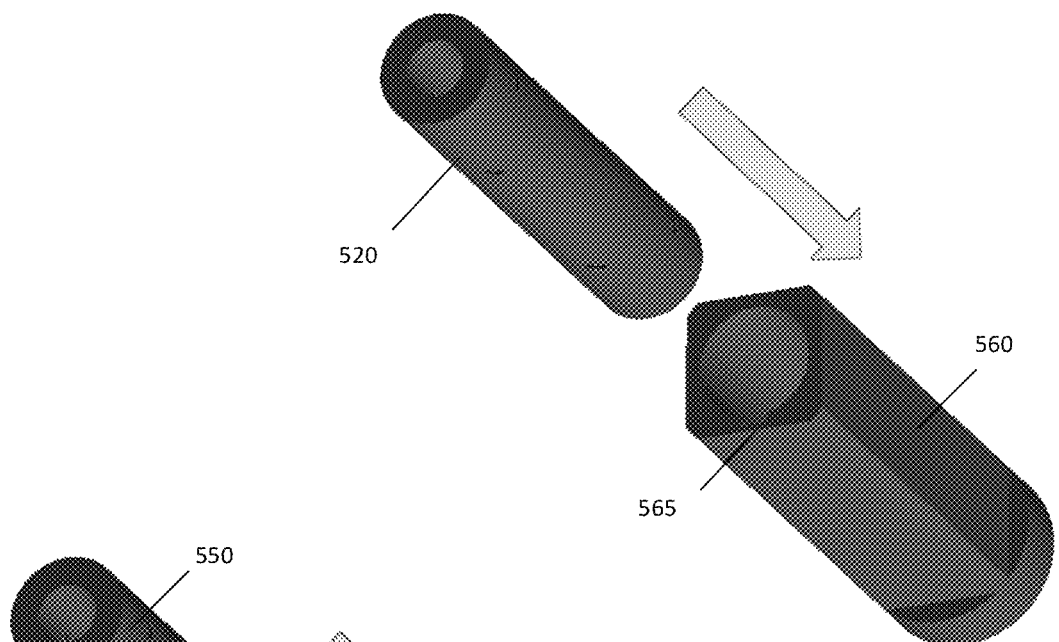
FIGS. 23A-23B illustrate an alternative example embodiment of the connection adapter, which can be used for a fixed connection of the attachment to the medical instrument, showing FIG. 23A a connection adapter with an outer axial extension that is received in a corresponding groove with the inner sleeve, and FIG. 23B the compatibility of the inner sleeve with a cylindrically symmetric connection adapter for rotatable instruments.
Figure 23A:
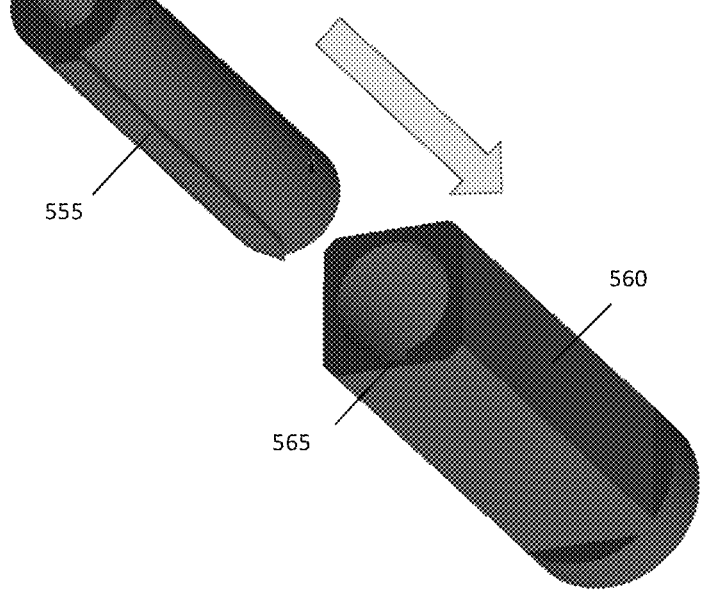

While the aforementioned embodiments provided rotatable marker attachments, a locking mechanism may be employed to a further modification of the above embodiment to prevent the rotation of certain medical instruments inside the attachment. An example implementation of this embodiment is shown in FIG. 23(a). Connection adapter 550 has a non-cylindrically symmetric feature for locking an orientation of the medical instrument within the bore of the internal sleeve 560. For example, as shown in the Figure, the non-symmetric feature may be a line of increased thickness 555 of the surface of connection adapter 550, on the outside surface, parallel to the cylinder axis, which is axially received in corresponding grooves 565 within internal sleeve 560. This embodiment also accommodates the previously described rotatable connection adapter 520, as shown in FIG. 23(b), because groove 565 in internal sleeve 560 does not impede rotation of connection adapter 520. Accordingly, the presence of such non-cylindrically symmetric features on a given connection adapter determines whether or not the corresponding medical instrument has a fixed or a rotatable connection to its marker assembly.

Another embodiment, shown in FIG. 24, employs mechanical clamping instead of the magnetic clamping to removably attach the marker assembly to the shaft 405 of the medical instrument 400. For example, as shown in the Figure, connection adapter 700 (which may be a metallic cylinder) can include a groove 705 for receiving a clamping fastener. Connection adapter 700 is placed and secured to the shaft 405 of the medical instrument 400, in a manner similar to the procedure descripted in FIG. 20. An additional calibration tool can be used to position the connection adapter 700 at a well-defined distance along the shaft from the tip 450 of the medical instrument 400, in a manner similar to the procedure shown in FIG. 22.

Marker assembly 710 has an insert hole 715 with the same diameter as the outside diameter of the connection adapter 700. Inside marker assembly 710 is a sliding plate 720 with a hole with the same diameter as the connector adaptor 700, as can be seen in FIG. 24(c). Two springs 730 hold this sliding plate 720 in a default position, shown in FIG. 24(c), in which axis of hole 725 is slightly off-centered relative to axis of hole 715 of marker assembly 710.

Figure 25B:
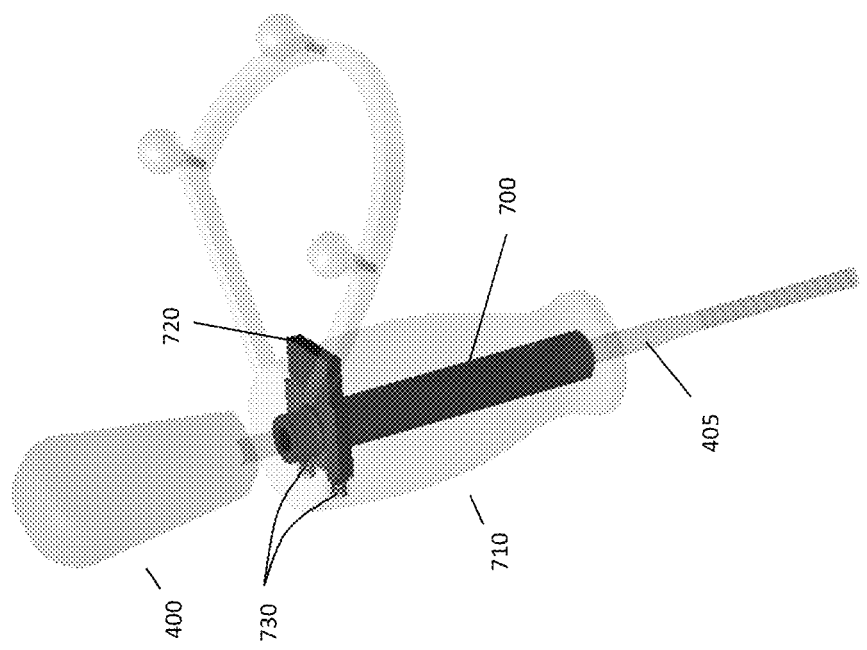
FIG. 25A-25B illustrate the mechanical clamping of the marker assembly from FIGS. 24A-24C onto the medical instrument, showing FIG. 25A a solid view and FIG. 25B a semi-transparent view.
Figure 25A:
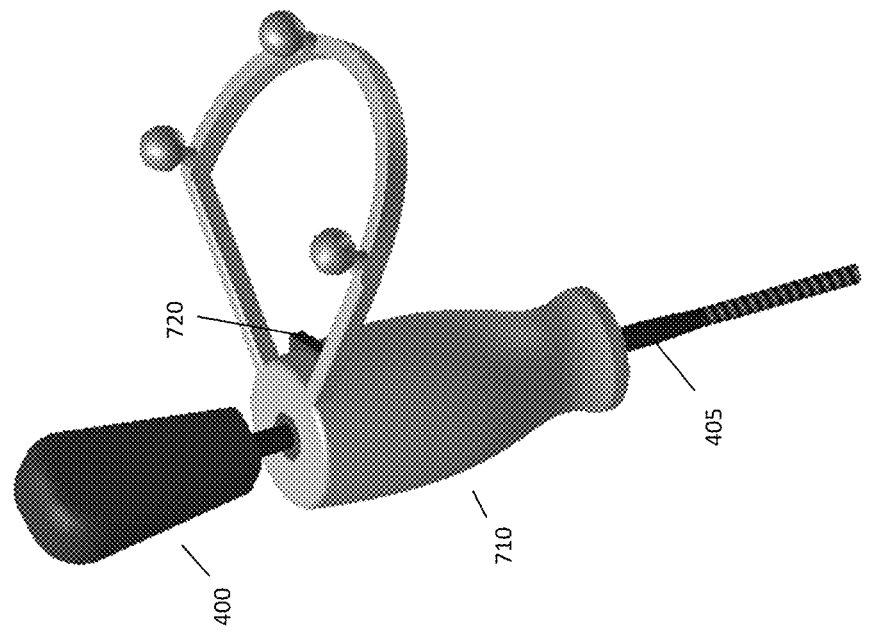
Figure 26A:
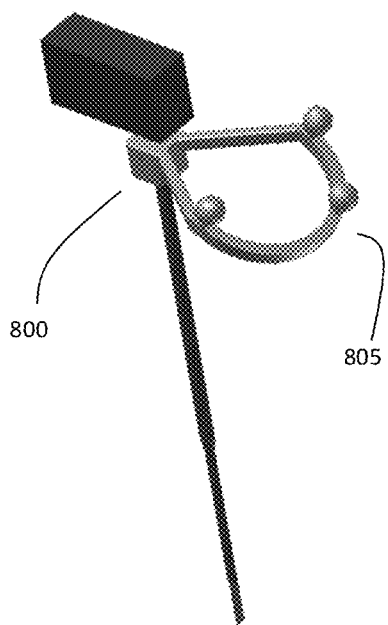
FIG. 26A-26F show a typical set of tracked medical tools that are used during medical procedures including FIG. 26A a pedicle finder, FIG. 26B awl, and FIGS. 26C-26E various taps, for which the instruments shown in FIG. 26C to 26E are connectable to removably attachable marker assembly FIG. 26F. In this example, the taps are used with the rotatable tracked attachment, while the pedicle finder and awl have a fixed attachment that is tracked.
Figure 26B:
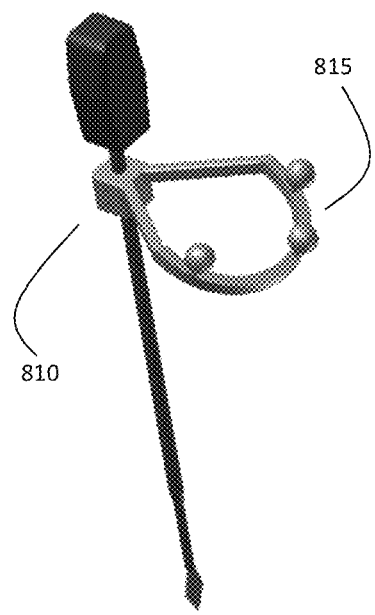
Figures 26C, 26D, 26E:
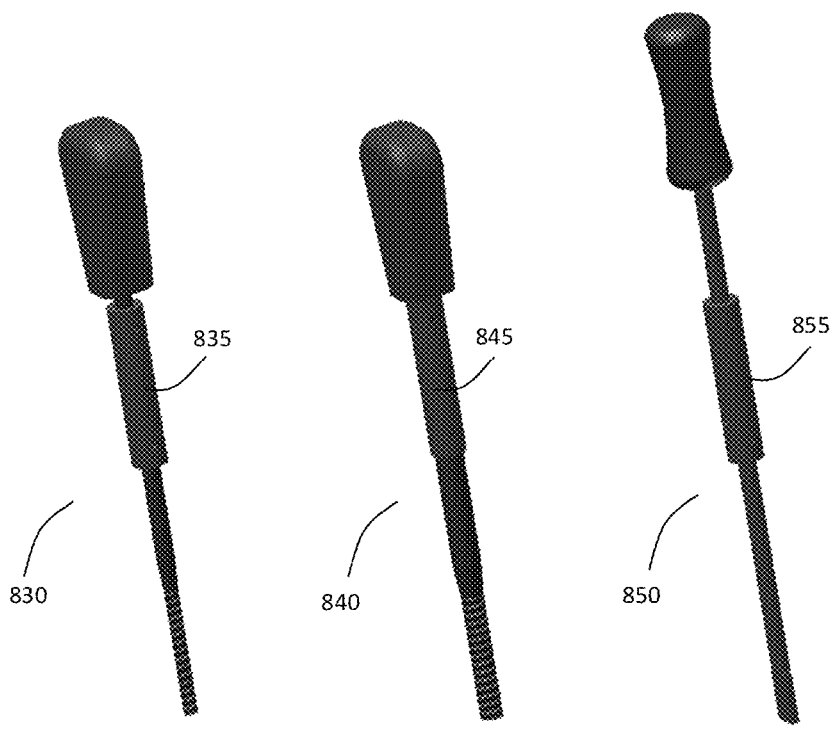
Figure 26F:
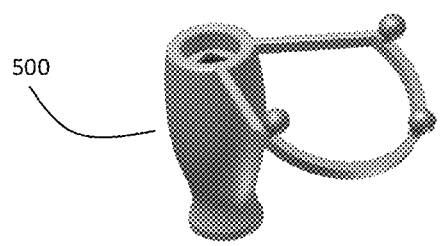
Figure 27A:
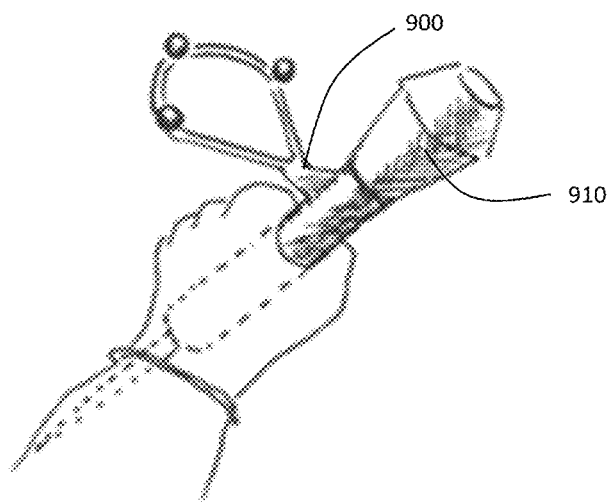
FIG. 27A shows a surgeon's hand holding the tracked tool with marker assembly in a suitable orientation for tracking. The marker assembly is at a suitable angulation from the rotatable tool shaft.
Figure 27B:
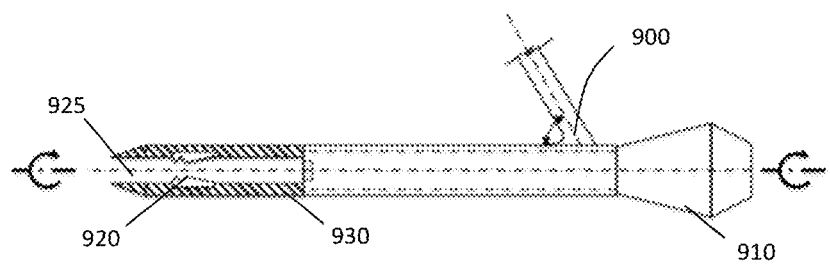
FIG. 27B shows a cut-away view of the tool shaft, showing one particular embodiment of a spring-locked rapid exchange system configured for use with multiple tool tips. Example tool tip selections include FIG. 27C awl, FIG. 27D pedicle finder, FIG. 27E tap, and FIG. 27F variable length screws pre-mounted on screwdriver bits. In the embodiment shown, the distance between the tip location and the marker assembly is constant for maintaining calibration after tool tip exchange.
Figure 27C:
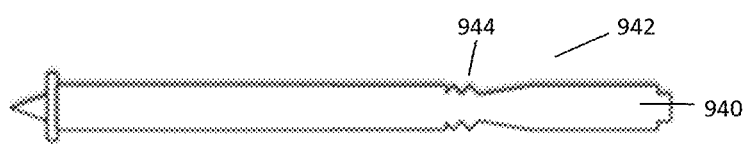
Figure 27D:
Figure 27E:
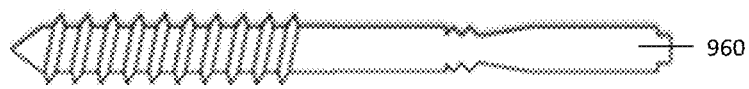
Figure 27F:
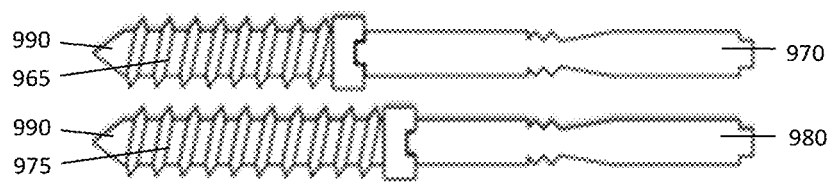

FIG. 25 illustrates the process of clamping connection adapter 700 within marker assembly 710, where connection adapter 700 is secured to shaft 405 of medical instrument 400. In order for marker assembly 710 to be able to receive connection adapter 700 in an unobstructed fashion within hole 715, the user presses sliding plate 720, thereby compressing springs 730 to align the axis of hole 725 with the axis of hole 715. After aligning the hole axes, connection adaptor 700 may be fully inserted into hole 715 of marker assembly 710. The user may then release sliding plate 720 to its default position, such that a proximal portion of sliding plate 720 engages groove 705 and secures the axial position of marker assembly 710.

The example clamping mechanism illustrated in FIGS. 24 and 25 is suitable for use with medical instruments which involve rotation during use. If it is preferable that a medical instrument should not be rotatable inside the attachment, a grove in a manner similar to one shown in FIG. 23 can be added to the device. It is also to be understood that the embodiment shown in FIGS. 24 and 25 is merely one example embodiment of a mechanical clamping mechanism, and that a wide range of other mechanical clamping mechanisms may be alternatively or additionally employed. For example, other detent mechanisms and/or fasteners (such as set screws) may be employed for mechanical clamping, with or without allowing rotation of connection adapter 700 within hole 715 of marker assembly 710. In other example implementations, the marker assembly may be removably secured to the shaft a suitable engagement mechanism such as mating threads or other interlocking features and/or securing the marker assembly using a friction fit.

The above embodiments can be combined to track an entire set of different medical instruments, for example, during surgery. One example is the set of medical instruments used during pedicle screw placement in spine surgery, shown in FIG. 26. This set can include an awl 800, a cutter 810, taps of different sizes 830 and 840, and screwdrivers 850. Since the awl 800 and the cutter 810 are normally twisted back and forth by a smaller rotation angle, two attachment designs with fixed connectors are used (FIGS. 15 (*a*) and (*b*)), which have different arrangements of markers (805 and 815) for instrument identification.

In this example, reflective spheres are used as markers for an optical tracking system. To reduce the impact of the marker attachment on the surgeon, a round-arc shape of the marker support is used. In addition, the attachments of the awl 800 and cutter 810 have the same dimensions, use a set of markers with a slightly different geometric arrangement, and are chosen to be as small as possible to reduce overall weight and visual impact on the surgical field of view.

In the present example embodiment, the surgeon may change marker assemblies between varying sizes of taps 830 and 840 and the screwdriver 850 quite frequently during the surgery. These instruments are also normally rotated several times around the instrument shaft. For these instruments the previously described exchangeable attachment device with a rotatable connection 500 is preferred. As can be seen in FIG. 26, each of these instruments is connected to a corresponding connection adapter 835, 845 and 855. The connection adapters in this illustration are placed with the calibration tool and have therefore the same distance to the tip of each respective instrument shaft.

Alternatively, in some situations, it is not necessary during navigated procedures for the surgeons to know the tip location of their tool for image guidance—the tool trajectory alone is sufficient. Therefore other medical tools, whose tip location has not been calibrated to the adaptor, can still be used for navigation, provided that the adaptor fits snugly around the bore of the tool such that the axis of the tool is aligned to the intended axis (trajectory) of the adaptor.

As mentioned above, for some marker types, the relative spacing of the markers becomes larger with the number of simultaneously tracked instruments. Two types of attachments have been described, one of which is specifically designed to fit one tool 100, and the other is an exchangeable attachment 500 that can be attached to multiple tools. In one example application, given the complete set of tools available to the surgeon, the exchangeable attachment may employ a marker arrangement where the spacing of the markers is large compared to the non-swappable marker attachment.

Such an embodiment may be useful when the exchangeable attachment is held relatively stationary by the surgeon, and only the tool itself is rotated, such that the arc of motion (sweep area) of the exchangeable attachment is small. Therefore, the marker support 510 can be relatively large, whereas for the non-swappable marker attachment, a large marker support would sweep out a much larger area when performing clockwise and anti-clockwise rotations, and would therefore be more obstructive. Furthermore, since the exchangeable attachment is held by the surgeon's hand, as shown in FIG. 16(*b*), the hand can obstruct part of the surgeon's view of field through the marker support. Therefore it may be useful to have a marker support with a larger opening for the exchangeable attachment.

Referring now to FIG. 27, an embodiment is illustrated in which a marker assembly 900 is attached to a rapid exchange handheld tool body 910, and where the shaft of the tool body 910 is configured for use with a plurality of exchangeable tool extensions, such as bits and/or fasteners. As shown in the Figure, a marker assembly 900 is secured (permanently or removably) to the rapid exchange tool 910. The marker assembly 900 may be provided according to any of the preceding embodiments.

The Figure illustrates an embodiment in which a spring-locked exchange mechanism 920 is employed for rapid exchange of a bit, fastener, combination thereof, or other exchangeable tool extension or combination thereof. For example, when employed with awl 940, a proximal portion 942 of the shaft of awl 940 is received within longitudinal bore 925 of shaft 930, and is secured in place by the spring-locked mechanism 920. Referring to FIGS. 27(*b*) and (*c*), the proximal portion 942 of awl 940 includes locking features 944 that cooperate with corresponding features in spring-locked mechanism 920.

Figure 28A:
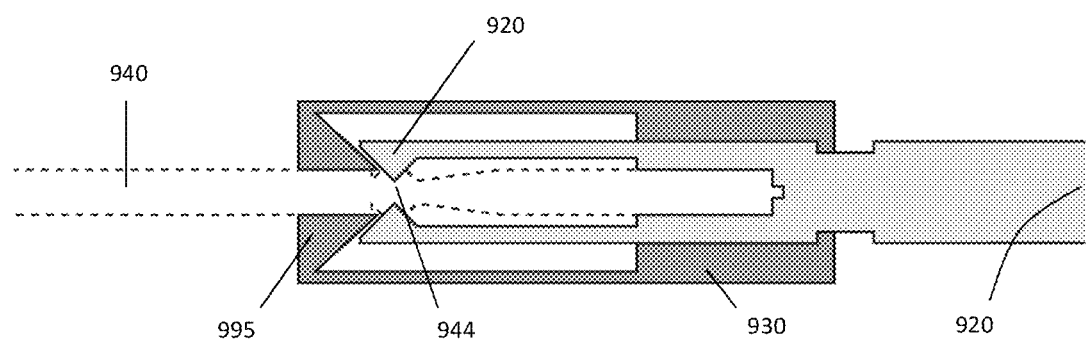
FIG. 28A-28B show a spring-locked exchange mechanism based on a spring collet for rapid exchangeable tool.
Figure 28B:
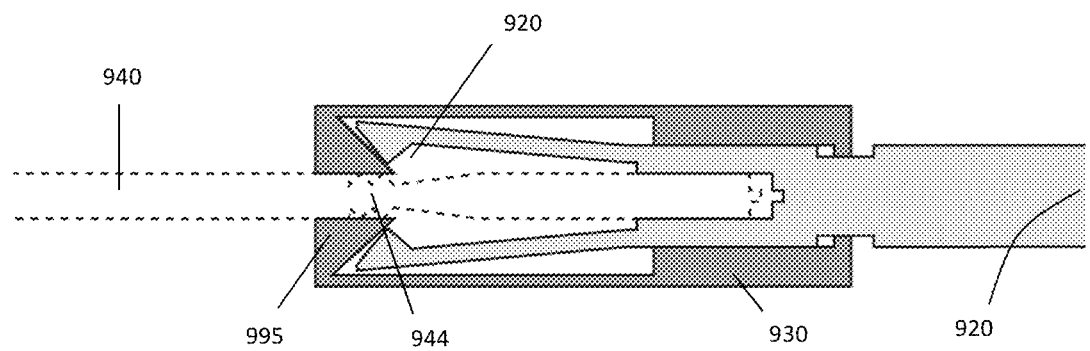

As shown in FIG. 28, the connector for the spring-locked exchange mechanism could be based on spring collet 920. The spring collet 920 clicks on the notch in the locking feature 944, when a tool extension 940, 950, 960, 970, or 980 is inserted into the rapid exchange tool 910 as shown in FIG. 28(*a*). The spring collet 920 is covered by a cylinder 930 which has a coned notch 995 in the inside pointing towards the spring collet 920. If the cylinder 930 is pressed towards the rapid exchangeable tool 910 as shown in FIG. 28(*b*), the coned notch 995 spreads the spring collet 920 and releases the tool extension 940, 950, 960, or 980. Afterwards another tool extension can be inserted into the rapid exchange tool 910. It is to be understood that the spring-locked mechanism illustrated in FIG. 27 is but one example implementation of a mechanism for removably securing a bit, fastener, or other functional element to rapid exchange tool 910. Other suitable and example implementations/mechanisms include thread-lock, magnetic, or pneumatic mechanisms. In one embodiment, mechanical contact between the outer shaft of the distal functional element and the inner bore 925 of shaft 930 utilizes compression and static friction. Other embodiments may include thread-lock, clip-lock, or pneumatic lock techniques.

According to one embodiment, the rapid exchange device described above may be employed for tracking fasteners of variable lengths, such as implantable screws 965 and 975 in FIG. 27(*f*). In one embodiment, screws 965 and 975 may be pre-mounted on screwdriver tips 970 and 980, where the lengths of screwdriver tips 970 and 980 are provided such that the tip locations 990 of the screws remain invariant relative to the position of marker assembly 900, thus preserving the calibration of location 990 under exchange of the different screwdriver and screw assemblies. This embodiment thus allows for tracking of the tip location of an exchangeable tool extension that includes a tool extension member (such as a screwdriver extension) and a functional member (such as a screw) removably attached to the tool extension member, where calibrated tracking may be maintained without the need for further calibration despite the use of functional members having different lengths.

FIGS. 27(*c*)-(*e*) illustrate other examples of exchangeable distal functional elements, include awl 940, pedicle finder 950, tap 960, with the location of the tip being invariant with respect to the marker assembly 900.

In other embodiments, the relative location between the tip 990 of the installed functional extension need not be fixed relative to the location of marker assembly 900, provided that the relative location is provided to the tracking system. For example, the tracking system may be pre-programmed with the relative locations of the distal tip of various exchangeable tool extensions, such that when a rapid exchange procedure is performed and a first exchangeable tool extension is removed and replaced with a second exchangeable tool extension, the system can select the appropriate calibration data for the second exchangeable tool extension from the pre-programmed calibration data.

The aforementioned marker assemblies and related devices may be employed for tracking medical instruments, for example, for computer-aided navigation of, or for, various medical methods and procedures. As mentioned above, many medical instruments, such as awls, cutters, screwdrivers or drills can be tracked using the aforementioned marker assemblies. This allows the use of navigation of, or to support, various surgeries including for example spine, hip, knee, and brain surgeries, where a direct view on the corresponding bone surface is possible. It is to be understood that the aforementioned examples may be for a wide variety of medical applications beyond surgery, such as guidance during the positioning of applicators for thermal therapies or navigation of biopsy needles.

Although the preceding embodiments have been described as example implementations involving medical applications, it is to be understood that the marker assemblies described above may be employed for the tracking of any handheld implement. Examples of other trackable handheld implements include tools and video game controllers, such as those that have a longitudinal shaft, longitudinal body, longitudinal member, or longitudinal axis.

For example, in one embodiment, the devices, systems and methods disclosed above can be adapted for the tracking of a video/computer game controller or handpiece. In one example implementation, a video game controller tracking system could be mounted on the ceiling above a group of players, who use tracked controllers such as styluses or other controllers to interact with different elements of the game.

The ceiling-mounted tracking system would enable the tracking, without obstruction, of all the players' controllers. In another example embodiment, the tracking system could be integrated with a monitor, such that during gameplay, a player points a tracked stylus at the tracking system in order to interact with the virtual components of the game (for example a hunting simulator).

In another example implementation, the tracked stylus could also be used in combination with a monitor, computer, and tracking cameras to be used a rehabilitation device, where the user would be asked to perform a set of spatial tasks such as connecting virtual dots or tracing out virtual objects projected onto the monitor showing the user, the virtual objects and their environment. This rehabilitation system could be used to track the progression/regression of patients with uncontrollable movement such as Parkinson's disease based on their interaction with the system as a function of time.

Therefore what is claimed is:

1. A trackable tool system comprising:
a plurality of exchangeable tool extensions, each exchangeable tool extension having a proximal portion, a distal functional end, and a longitudinal axis;
a handheld body adapted to detachably secure each exchangeable tool extension at said proximal portion thereof, such that one exchangeable tool extension may be secured to said handheld body at any given time;
a support member connected to said handheld body; and
one or more tracking markers affixed to said support member, said tracking markers defining a marker plane;
wherein said distal functional end of each exchangeable tool extension is located such that when a first exchangeable tool extension, secured to said handheld body as an operative tool extension, is replaced with a second exchangeable tool extension, with said second exchangeable tool extension becoming the operative tool extension secured to said handheld body, a location of a distal functional end of the operative tool extension remains invariant relative to said one or more tracking markers before and after replacement of said first exchangeable tool extension with said first exchangeable tool extension, said one or more tracking markers thereby being suitable for locating a three-dimensional position of said distal functional end of said second exchangeable tool extension and an orientation said second exchangeable tool extension by a tracking system without recalibration.

2. The trackable tool system according to claim 1 wherein said handheld body comprises a locking mechanism for detachably securing said exchangeable tool extensions.

3. The trackable tool system according to claim 2 wherein the locking mechanism is a spring-locked mechanism.

4. The trackable tool system according to claim 3 wherein a distal portion of said handheld body has a longitudinal bore defined therein, and wherein the spring-locked mechanism comprises a spring collet located within the longitudinal bore for engaging with each exchangeable tool extension when each exchangeable tool extension is inserted into the longitudinal bore.

5. The trackable tool system according to claim 4 wherein each exchangeable tool extension comprises a locking feature that engages with the spring collet when each exchangeable tool extension is inserted into the longitudinal bore.

6. The trackable tool system according to claim 2 wherein the locking mechanism is selected from the group consisting of a thread-lock locking mechanism, clip-lock locking mechanism, magnetic locking mechanism, and pneumatic mechanism locking mechanism.

7. The trackable tool system according to claim 1 wherein one or more of said exchangeable tool extensions is a single member.

8. The trackable tool system according to claim 1 wherein one or more of said exchangeable tool extensions comprises:
a tool extension member configured to be detachably secured to said handheld body; and
a functional member detachably secured to said tool extension member at a distal end thereof.

9. The trackable tool system according to claim 8 wherein the tool extension member is a screwdriver extension member, and wherein the functional member is a screw.

10. The trackable tool system according to claim 9 wherein the screw is pre-mounted on the screwdriver extension member.

11. The trackable tool system according to claim 8 wherein said functional member is a fastener.

12. The trackable tool system according to claim 1 wherein said marker plane is not parallel to the longitudinal axis, such that said tracking markers are visible to an overhead tracking system.

13. The trackable tool system according to claim 1 wherein the exchangeable tool extensions comprise one or more of an exchangeable awl extension, an exchangeable pedicle finder, and an exchangeable tap.

14. A system for tracking one or more handheld implements, comprising:
a trackable handheld device according to claim 1;
a tracking system configured to detect a signal associated with each tracking marker, wherein said tracking system is positioned in a substantially overhead configuration; and
a processor configured to receive said signals and to calculate a relative position and orientation of said handheld implement based on said signals, when said support member is secured to said handheld implement.

15. A trackable tool system comprising:
a plurality of exchangeable tool extensions, each exchangeable tool extension having a proximal connection feature, a distal functional end, and a longitudinal axis, each exchangeable tool extension being absent of a handle;
a handheld body comprising:
an elongate handle configured to be gripped by a hand of a user;
a support member extending from said handheld body;
one or more tracking markers affixed to said support member, said one or more tracking markers defining a marker plane;
a connection mechanism, residing at a distal portion of said handheld body, distalward of said elongate handle, said connection mechanism being configured to detachably secure, via engagement with said connection feature, any one of said plurality of exchangeable tool extensions thereto at any given time.

16. The system according to claim 15, wherein two or more exchangeable tool extensions have different lengths.

17. The system according to claim 15 wherein said connection mechanism comprises a locking mechanism for detachably locking said one or more exchangeable tool extensions to said handheld body.

18. The system according to claim 17 wherein the locking mechanism is a spring-locked mechanism.

19. The system according to claim 18 wherein said distal portion of said handheld body has a longitudinal bore defined therein, and wherein the spring-locked mechanism comprises a spring collet located within the longitudinal bore for engaging with each exchangeable tool extension when each exchangeable tool extension is inserted into the longitudinal bore.

20. The system according to claim 19 wherein each exchangeable tool extension comprises a locking feature that engages with the spring collet when each exchangeable tool extension is inserted into the longitudinal bore.

21. The system according to claim 17 wherein the locking mechanism is selected from the group consisting of a thread-lock locking mechanism, clip-lock locking mechanism, magnetic locking mechanism, and pneumatic mechanism locking mechanism.

22. The system according to claim 15 wherein one or more of said exchangeable tool extensions is a single member.

23. The system according to claim 15 wherein one or more of said exchangeable tool extensions comprises:
a tool extension member configured to be detachably secured to said handheld body; and
a functional member detachably secured to said tool extension member at a distal end thereof.

* * * * *